(12) United States Patent
Trepel et al.

(10) Patent No.: US 9,389,223 B2
(45) Date of Patent: Jul. 12, 2016

(54) PHARMACODYNAMIC ASSAYS

(75) Inventors: Jane Trepel, Bethesda, MD (US); Eun Joo Chung, Rockville, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 980 days.

(21) Appl. No.: 11/467,080

(22) Filed: Aug. 24, 2006

(65) Prior Publication Data

US 2007/0054260 A1    Mar. 8, 2007

Related U.S. Application Data

(63) Continuation of application No. PCT/US2005/006236, filed on Feb. 25, 2005.

(60) Provisional application No. 60/548,794, filed on Feb. 27, 2004.

(51) Int. Cl.
| | |
|---|---|
| *C12N 15/85* | (2006.01) |
| *G01N 33/537* | (2006.01) |
| *C12Q 1/34* | (2006.01) |
| *C12Q 1/44* | (2006.01) |
| *G01N 33/50* | (2006.01) |

(52) U.S. Cl.
CPC ............... *G01N 33/537* (2013.01); *C12Q 1/34* (2013.01); *C12Q 1/44* (2013.01); *G01N 33/5011* (2013.01); *G01N 2500/00* (2013.01)

(58) Field of Classification Search
CPC .......... C12Q 1/34; C12Q 1/44; G01N 33/537; G01N 33/5011
See application file for complete search history.

(56) References Cited

U.S. PATENT DOCUMENTS

| 5,447,837 | A  * | 9/1995 | Urnovitz ........................... 435/5 |
| 6,280,967 | B1 * | 8/2001 | Ransom et al. ................. 435/29 |
| 2005/0153302 | A1 * | 7/2005 | Pruitt et al. ....................... 435/6 |
| 2008/0102476 | A1 * | 5/2008 | Karlsson et al. ............... 435/7.2 |

FOREIGN PATENT DOCUMENTS

| EP | 1403639 A1 | 3/2004 |
| WO | WO-0011476 A1 | 3/2000 |
| WO | WO-2005007158 A1 | 1/2005 |
| WO | WO-2005085864 A1 | 9/2005 |

OTHER PUBLICATIONS

Kwon et al. Apicidin, a histone deacetylase inhibitor, induces apoptosis and Fas/Fas ligand expression in human acute promyelocytic leukemia cells. J. Biol. Chem. 277(3): 2073-2080, 2002.*

Boggild et al. Localization of post-translationally modified alpha-tubulin and pseudocyst formation in tritrichomonads. Parasitol. Res. 88: 468-474, 2002.*

Nimmanapalli et al. Histone deacetylase inhibitor LAQ824 both lowers expression and promotes proteasomal degradation of Bcr-Abl and induces apoptosis of imatinib mesylate-sensitive or -refractory chronic myelogenous leukemia-blast crisis cells. Cancer. Res. 63: 5126-35, 2003.*

Enright et al. Epigenetic Characteristics of Bovine Donor Cells for Nuclear Transfer: Levels of Histone Acetylation. Bio. of Reproduction 69: 1525-1530, 2003.*

Brown, A. , et al., "Composite Microtubules of the Axon: Quantitative Analysis of Tyrosinated and Acetylated Tubulin Along Individual Axonal Microtubules", *Journal of Cell Science*, 104 (Pt 2), (Feb. 1993), pp. 339-352.

Hashiguchi, N. , et al., "Enhanced Expression of Heat Shock Proteins in Leukocytes from Trauma Patients", *The Journal of Trauma*, 50 (1), (Jan. 2001), pp. 102-107.

He, L. , et al., "Variation of Heat Shock Protein 70 through the Cell Cycle in HL-60 Cells and its Relationship to Apoptosis", *Experimental Cell Research*, 232 (1), (Apr. 10, 1997), pp. 64-71.

Jaboin, J. , et al., "MS-27-275, an Inhibitor of Histone Deacetylase, Has Marked in vitro and in Vivo Antitumor Activity against Pediatric Solid Tumors", *Cancer Research*, 62 (21), (Nov. 1, 2002), pp. 6108-6115.

Kim, J. , et al., "Changes in Histone Acetylation during Mouse Oocyte Meiosis", *The Journal of Cell Biology*, 162 (1), (Jul. 7, 2003), pp. 37-46.

Trujillo, M , et al., "Pharmacodynamic Impact of the Orally Bioavailable Histone Deacetylase Inhibitor MS-275 on Acute Myeloid Leukemia", *Biosis, 43rd Annual Meeting of the American Society of Hematology, Part 1*, (Dec. 7, 2001), pp. 1-2.

Gojo, Ivana, et al., "Phase 1 and pharmacologic study of MS-275, a histone deacetylase inhibitor, in adults with refractory and relapsed acute leukemias", *Blood 109, No. 7* (Apr. 1, 2007), 2781-2790.

Kummar, Shivaani, et al., "Phase I Trial of MS-275, a Histone Deacetylase Inhibitor, Administered Weekly in Refractory Solid Tumors and Lymphoid Malignancies", *Clin. Cancer Res. 2007*; 13 (18) (Sep. 15, 2007), 5411-5417.

Aron et al., "Depsipeptide (FR901228) induces histone acetylation and inhibition of histone deacetylase in chronic lymphocytic leukemia cells concurrent with activation of caspase 8-mediated apoptosis and down-regulation of c-FLIP protein", *Blood* 102:652-658 (2003).

Kelly et al,, "Phase I Clinical Trial of Histone Deacetylase inhibitor: Suberoylanilide Hydroxamic Acid Administered Intravenously", *Clin. Cancer Res.* 9:3578-3538 (2003).

Zhang et al., "Differential Expression of Histone Post-Translational Modifications in Acute Myeloid and Chronic Lymphocytic Leukemia Determined by High-Pressure Liquid Chromatography and Mass Spectrometry", *J. Am. Soc, Mass. Spectrom*, 15:77-86 (2004).

* cited by examiner

*Primary Examiner* — Michele K Joike
(74) *Attorney, Agent, or Firm* — Locke Lord LLP; Gabriel J. McCool

(57) ABSTRACT

The invention provides methods for quickly and easily screening mixed cell samples for a pharmacodynamic effect to a drug or test agent.

31 Claims, 11 Drawing Sheets

FLOW CYTOMETRIC ANALYSIS OF PROTIEN ACETYLATION IN A BONE MARROW ASPIRATE OF A LEUKEMIA PATIENT PRE- AND POST-TREATMENT WITH MS-275

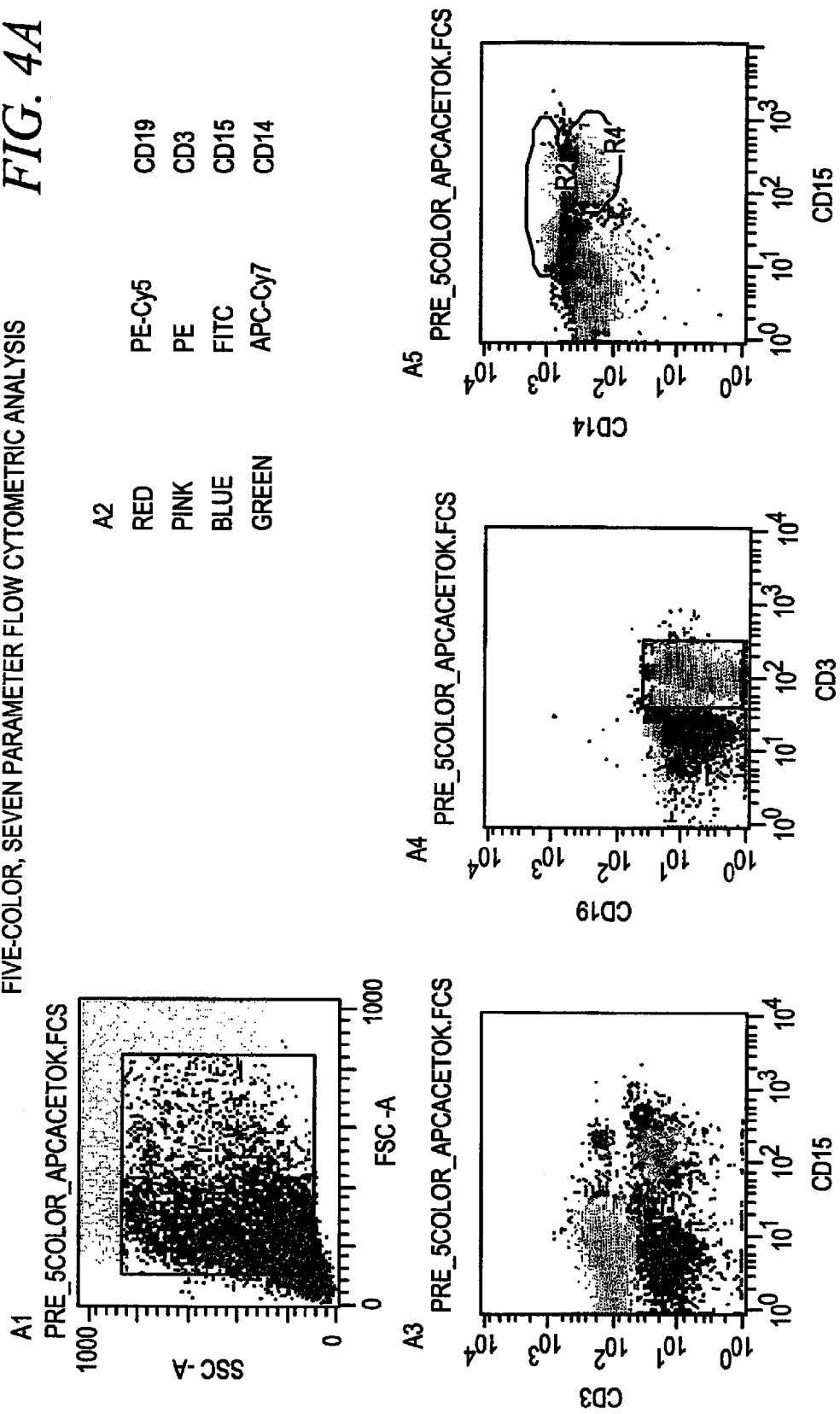

PHARMACODYNAMIC ASSAYS

This application is a continuation under 35 U.S.C. 111(a) of International Application No. PCT/US2005/006236 filed Feb. 25, 2005 and published in English as WO 2005/085864 on Sep. 15, 2005, which claimed the benefit of U.S. Provisional Application Ser. No. 60/548,794, filed Feb. 27, 2004, the contents of which applications and publication are incorporated herein in their entireties.

GOVERNMENT SUPPORT

The invention described herein was developed with support from the National Institutes of Health. The U.S. Government has certain rights in the invention.

FIELD OF THE INVENTION

The invention relates to fast, simple assays for detecting the pharmacodynamic effects of drugs in small samples of mixed populations of cells, for example, in small blood samples.

BACKGROUND OF THE INVENTION

Initial screening for the pharmacodynamic effects of drugs typically involves western analysis and/or immunocytochemical observation of the drug response in a selected number of relevant cell types or biological samples. However, such procedures are labor intensive and provide limited information on only one or two variables that relate to the pharmacodynamic effects of the drug. Moreover, the effects of drug combinations cannot easily be understood by examination of western blots or by viewing a limited number of cells through a microscope. Hence, new procedures are needed that allow analysis of multiple pharmacodynamic markers in multiple cells at once. Such procedures would better reflect the overall response of multiple cell types to the drug(s).

Pharmacodynamic drug effects are also better understood when large number of samples from different people are tested. However, collection, storage and testing of such large numbers of samples can be burdensome, particularly if the samples must be extensively purified or manipulated before the actual test is performed. For example, researchers frequently study the effects of drugs on lymphocytes. However, separation of lymphocytes from whole blood typically is done by Ficoll gradient separation, which requires technical expertise and expensive equipment. Hence, screening procedures are needed that do not require extensive manipulation or purification of samples prior to testing.

SUMMARY OF THE INVENTION

The invention provides pharmacodynamic assay methods for easily screening large numbers of mixed cell samples. Several pharmacodynamic parameters and/or the effects of combinations of drugs can be monitored at once. Only small sample volumes of mixed cell populations are needed for the present methods. For example, volumes of whole blood samples as small as about fifty microliters can readily be tested by the methods of the invention. No purification of the different cell types within the sample is required, first, because it is desirable to observe the effect of the drug(s) on multiple cell types and, second, because the present methods can simultaneously be used to identify different cell types and observe how they are responding to the drug(s). The inventive methods are therefore useful for quickly screening large numbers of blood samples to identify useful drugs and their pharmacodynamic effects upon various cell types.

In some embodiments, the invention provides methods for detecting and quantifying protein acetylation levels within the eukaryotic cells. According to the invention, the degree of acetylation in such a sample is one measure of whether a drug (e.g. a deacetylase inhibitor) can influence acetylation in the subject from which the sample was obtained.

Thus, one aspect of the invention is a method of monitoring a pharmacodynamic response of a mixed population of eukaryotic cells to a drug. The method involves: (a) obtaining a mixed population of cells that has been exposed in vitro or in vivo to a drug to form a first test mixture; (b) contacting the first test mixture with a reagent that can detect a pharmacodynamic response to the drug to form a second test mixture; and (c) observing whether cells in the second test mixture exhibit the pharmacodynamic response by flow cytometry. In some embodiment, the method can further involve quantifying the pharmacodynamic response of the cells to the drug. Quantifying the pharmacodynamic response of the cells to the drug can include calculating what proportion of cells in the mixed population exhibit the pharmacodynamic response. Alternatively, quantifying the pharmacodynamic response of the cells to the drug can involve calculating an increase or decrease in fluorescence signal during flow cytometry relative to one or more suitable controls. One example of a suitable control is a sample of the same mixed population of cells subjected to the method without exposure to the drug. Another example of a suitable control is a sample of the same mixed population of cells subjected to the method after being exposed to a drug that is known to produce the pharmacodynamic response. The mixed population of cells can, for example, be human blood, animal blood or other cells samples including cell lines available in the art. Only small volumes are needed to perform the methods of the invention, for example, volumes ranging from about 25 microliters to about 150 microliters.

Reagents that can detect a pharmacodynamic response include, for example, antibody preparations that can bind to a pharmacodynamic marker, where the antibodies have a detectable label directly linked thereto or where the antibodies indirectly associate with a detectable label, for example, by binding to a secondary antibody that is labeled.

In some embodiments, the pharmacodynamic marker is acetylated protein. When the pharmacodynamic marker is an acetylated protein, the drug can, for example, be a deacetylase inhibitor. Examples of deacetylase inhibitors whose pharmacodynamic responses can be monitored include MS-275, trichostatin A, trapoxin, sodium butyrate, apicidin, sodium phenylbutyrate, phenylacetate, depsipeptide, 3-bromopropionate, valproic acid, tributyrin, suberoylanilide hydroxamic acid (SAHA), m-carboxycinnamic acid bishydroxamic acid (CBHA), oxamflatin, pyroxamide, CHAP, depsipeptide (FK228), NVP-LAQ824, CI-994, PXD101, apicidin-derived quinolone derivatives and combinations thereof. In another embodiment, the pharmacodynamic marker is Hsp70 or acetylated tubulin. When the pharmacodynamic marker is Hsp70 or acetylated tubulin, the drug can, for example, be an anti-cancer drug.

In some embodiments, the mixed population of cells can be exposed to more than one drug and the effects of all such drugs can be monitored simultaneously.

The methods of the invention can readily be adapted to include observing which cell types exhibit the pharmacodynamic response, observing in what cell cycle stage the cells exhibit the pharmacodynamic response, observing whether some of the cells are undergoing apoptosis, or a combination thereof.

Another aspect of the invention is a method of identifying whether a test agent has a pharmacodynamic response in a mixed population of eukaryotic cells. This method involves: (a) obtaining a mixed population of cells that has been exposed in vitro or in vivo to a test agent to form a first test mixture; (b) contacting the first test mixture with a reagent that can detect a selected pharmacodynamic response to thereby form a second test mixture; and (c) observing whether cells in the second test mixture exhibit the pharmacodynamic response by flow cytometry.

Another aspect of the invention is a method of monitoring deacetylation of a mixed population of eukaryotic cells exposed to a deacetylase inhibitor. This method involves: (a) obtaining a mixed population of eukaryotic cells exposed in vitro or in vivo to the deacetylase inhibitor to form a first test mixture; (b) contacting the first test mixture with a reagent that can detect protein acetylation to form a second test mixture; and (c) quantifying protein acetylation in the second test mixture by flow cytometry.

Another aspect of the invention is a method of monitoring a pharmacodynamic response of a small sample of whole blood to a drug. This method involves: (a) obtaining a small sample of whole blood exposed in vitro or in vivo to a drug to form a first test mixture; (b) contacting the first test mixture with a reagent that can detect a pharmacodynamic response to the drug to form a second test mixture; and (c) observing whether cells in the second test mixture exhibit the pharmacodynamic response by flow cytometry.

Another aspect of the invention is a method of monitoring deacetylation in a small sample of whole blood exposed to a deacetylase inhibitor. This method involves: (a) obtaining a small sample of whole blood exposed in vitro or in vivo to the deacetylase inhibitor to form a first test mixture; (b) contacting the first test mixture with a reagent that can detect protein acetylation to form a second test mixture; and (c) quantifying protein acetylation in the second test mixture by flow cytometry.

Another aspect of the invention is a method of monitoring deacetylation in a small sample of whole blood exposed to MS-275. This method involves: (a) obtaining a small sample of whole blood exposed in vitro or in vivo to MS-275 to form a first test mixture; (b) contacting the first test mixture with a reagent that can detect protein acetylation to form a second test mixture; and (c) quantifying protein acetylation in the second test mixture by flow cytometry.

Another aspect of the invention is a method of monitoring deacetylation of a mixed population of eukaryotic cells exposed to a deacetylase inhibitor. This method involves: (a) obtaining a mixed population of eukaryotic cells exposed in vitro or in vivo to the deacetylase inhibitor to form a first test mixture; (b) contacting the first test mixture with a reagent that can detect protein acetylation to form a second test mixture; and (c) quantifying protein acetylation in the second test mixture by fluorimetry.

Another aspect of the invention is a method of quantifying protein acetylation in a small sample of whole blood. This method involves: (a) fixing cells from the whole blood with 0.4% paraformaldehyde in phosphate buffered saline to generate fixed cells; (b) incubating the fixed cells with 0.4% Triton X-100 in phosphate buffered saline to generate permeabilized cells; (c) reacting the permeabilized cells with an anti-acetylated lysine antibody preparation to form a complex between the permeabilized cells and the anti-acetylated lysine antibody; and (d) quantifying protein acetylation using flow cytometry by observing a signal from a label associated with the anti-acetylated lysine antibody.

In most instances no purification of specific cell types from the small sample of whole blood need be performed.

Another aspect of the invention is a kit that includes a reagent for detecting a pharmacodynamic response and instructions for using the reagent to detect or quantify the pharmacodynamic response in a mixed cell sample by flow cytometry. The reagent is used to detect and quantify the pharmacodynamic response. Such reagent can, for example, be an anti-acetylated lysine antibody preparation for detecting protein acetylation, an anti-Hsp70 antibody preparation or an anti-acetylated tubulin antibody preparation for detecting a pharmacodynamic response to an anti-cancer agent, a reagent used for detecting apoptosis or a combination thereof. The kit can also include alcohol swabs, a sharp object for performing a finger prick, a capillary tube or a vacutainer. In many embodiments, the kit can also include a solution for fixing or permeabilizing cells within a cell sample. The kit can be is packaged or designed for obtaining and detecting a pharmacodynamic response in one or more small samples of whole blood. In some embodiments, the kit is designed for obtaining and detecting a pharmacodynamic response in many small samples of whole blood. Sample sizes can be small, for example, small samples of blood can be used that are about 25 to about 150 microliters.

DESCRIPTION OF THE DRAWINGS

FIG. 1A-E illustrate that concentration-dependent protein acetylation occurs in healthy donor peripheral blood mononuclear cells that were incubated in vitro with the histone deacetylase inhibitor MS-275. The MS-275 compound is N-(2-aminophenyl)-4-[N-(pyridin-3-ylmethoxycarbonyl) aminomethyl]benzamide. See, Saito et al., Proc. Natl. Acad. Sci. USA 96, 4592-4597 (1999). As shown in FIG. 1A, the peak of fluorescence reflecting acetylated lysine levels observed for cells treated with no MS-275 is centered over a lower fluorescence reading than the peak of cells treated with 10 nM MS-275 (FIG. 1B) and especially the peak of cells treated with 1.0 µM MS-275 (FIG. 1C). FIG. 1D provides a negative control showing the fluorescence of cells treated with normal rabbit antibodies. FIG. 1E provides a merged graph showing the amount of acetylated lysine in populations of control cells (left-most peak), of cells treated with 10 nM MS-275 (middle peak) and of cells treated with 1.0 µM MS-275 (right-most peak).

FIG. 2A-E show that in vivo administration of the histone deacetylase inhibitor MS-275 gives rise to concentration-dependent protein acetylation in peripheral blood mononuclear cells. Whole blood was obtained before MS-275 administration and then 24 hours after MS-275 treatment. FIG. 2A-B show the fluorescence detected from CD3 labeled cells on the y-axis and the fluorescence detected from anti-acetylated lysine residues on the x-axis. The fluorescence pattern for cells obtained before MS-275 treatment (FIG. 2A) was low and diffuse. However, as shown in FIG. 2B, acetylated lysine fluorescence increases after MS-275 treatment. Moreover, FIG. 2A-B indicate that there are positive and negative populations of CD3-positive cells: those that express CD-3 are T cells while non-T cells express no CD3 and form a smaller population of cells nearer the x-axis. FIG. 2D further illustrates the amount of acetylated lysine detected in cells isolated after MS-275 treatment is greater than that detected before treatment (FIG. 2C). FIG. 2E provides a graph showing fluorescence from both pre-treatment (left peak) and post-treatment (right peak) cells.

FIG. 3A-C illustrate that concentration-dependent protein acetylation occurs in bone marrow aspirates of leukemia patients treated in vivo with the histone deacetylase inhibitor MS-275. The acetylation of bone marrow aspirates is shown by flow cytometry analysis prior to treatment (FIG. 3A) and after treatment with MS-275 (FIG. 3B). FIG. 3C provides a graph showing fluorescence from both pre-treatment (unshaded peak) and post-treatment (shaded peak) cells. These data illustrate that the assay can be used for detection of a drug response in bone marrow aspirates.

FIGS. 4A and 4B illustrate that the methods of the invention can be used not only for quantifying total acetylation but also for correlating the level of such acetylation with the presence or absence of cell-type specific markers.

FIG. 4A1-5 illustrate that a large variety of cells types can be detected in samples by the present methods, as shown by the results of a five-color, seven parameter flow cytometric analysis. This assay was performed by incubating peripheral blood with antibody preparations directed against different markers and then detecting the presence of those markers using flow cytometric procedures. The markers employed were the B cell-specific CD19 marker (using a PE-Cy5 label), the T cell-specific CD3 marker (using a PE label), the granulocyte/monocyte CD15 marker (using a FITC label) and the monocyte-specific CD14 marker (using an APC-Cy7 label). A scatter gram is provided in FIG. 4A1, showing the forward (FSC-A) and side (SSC-A) light scattering of this mixed population of cells. FIG. 4A2 shows the fluorescence colors associated with the fluorophore types on antibody preparations used to detect CD19, CD3, CD15 and CD14. FIG. 4A3 shows the fluorescence of cells displaying the CD15 marker along the x-axis and fluorescence of cells displaying the CD3 marker along the y-axis. The CD15 marker is most visible in the group of cells at the lower right of FIG. 4A3 (blue in the original). FIG. 4A4 provides a graph showing fluorescence of cells displaying the CD3 marker along the x-axis and fluorescence of cells displaying the CD19 marker along the y-axis. CD19 cells (red in original) are much more predominant on the left, whereas CD3 cells (boxed in cells; pink in original) are much more predominant on the right. FIG. 4A5 is a graph showing fluorescence of cells displaying the CD15 marker along the x-axis and fluorescence of cells displaying the CD14 marker along the y-axis. CD15 cells (R4 circled cells; blue in original) are much more predominant on the lower right, whereas CD14 cells (R2 circled cells; green in original) are much more predominant on the right.

FIG. 4B1-4 illustrate the effects of the deacetylase inhibitor MS-275 upon the various cell types, as observed by a five-color, seven parameter flow cytometric analysis of protein acetylation using flow cytometric procedures. The cells were stained with cell-specific markers as described for FIG. 4A1-5 and simultaneously stained for acetylated lysine. FIGS. 4B3 and 4B4 show that cells expressing both low and higher levels of the granulocyte/monocyte CD15 marker exhibit increased acetylation after treatment with the MS-275 deacetylase inhibitor (FIG. 4B4) compared to cells that did not receive MS-275 (FIG. 4B3). The CD15-expressing cells are found mostly within the upper right quadrant of FIG. 4B3-4. FIGS. 4B1 and 4B2 show that cells positive and negative for expression of the T cell-specific CD3 marker exhibit increased acetylation after treatment with the MS-275 deacetylase inhibitor (FIG. 4B2) compared to cells that did not receive MS-275 (FIG. 4B1). The CD3-expressing cells are most visible in the lower right quadrant of FIG. 4B1, and after MS-275 treatment shift upward into part of the upper right quadrant of FIG. 4B2.

FIG. 5A-B illustrate that the pharmacodynamic effects of different drugs can be separately monitored using the methods of the invention. The drugs employed were the anti-cancer drug 17-allylaminogeldanamycin (17-AAG) and the deacetylase inhibitor trichostatin A (TSA). The effects of 17-AAG can be monitored by observing whether the levels of Hsp70 change—increased Hsp70 levels indicate that the 17-AAG drug is having an effect upon the cells. As shown in FIG. 5A, increased levels of Hsp70 were detected using the methods of the invention after treatment of the cells with 17-AAG. The effect of TSA on leukemia cells can be seen in FIG. 5B. While TSA is a generalized deacetylase inhibitor, the effect of TSA in this study was assessed by observing whether a change in the levels of tubulin acetylation (using anti-acetylated tubulin antibodies) occurred. FIG. 5B shows that increased levels of acetylated tubulin were apparent after treatment of the cells with TSA.

As shown in FIG. 6C-D, both Hsp70 and acetylated tubulin levels, respectively, increased in cells treated with 17-AAG and TSA. The dot blots shown in FIG. 6A-B confirm that the population of cells exhibited increased fluorescence for both the Hsp70 and acetylated tubulin markers, respectively.

As shown in FIG. 7C-D, both Hsp70 and acetylated protein levels, respectively, increased in cells treated with 17-AAG and MS-275. The three-dimensional graph shown in FIG. 7B confirms that cells treated with 17-AAG and MS-275 exhibit increased fluorescence for both the Hsp70 and acetylated proteins compared to the non-treated cells shown in FIG. 7A.

FIG. 8C-D illustrates the subcellular localization of acetylated proteins in cells treated and stained as in FIG. 8B. FIG. 8C shows a cell with predominantly nuclear staining, whereas FIG. 8D shows a cell with predominantly cytoplasmic staining.

DETAILED DESCRIPTION OF THE INVENTION

Figure 1:
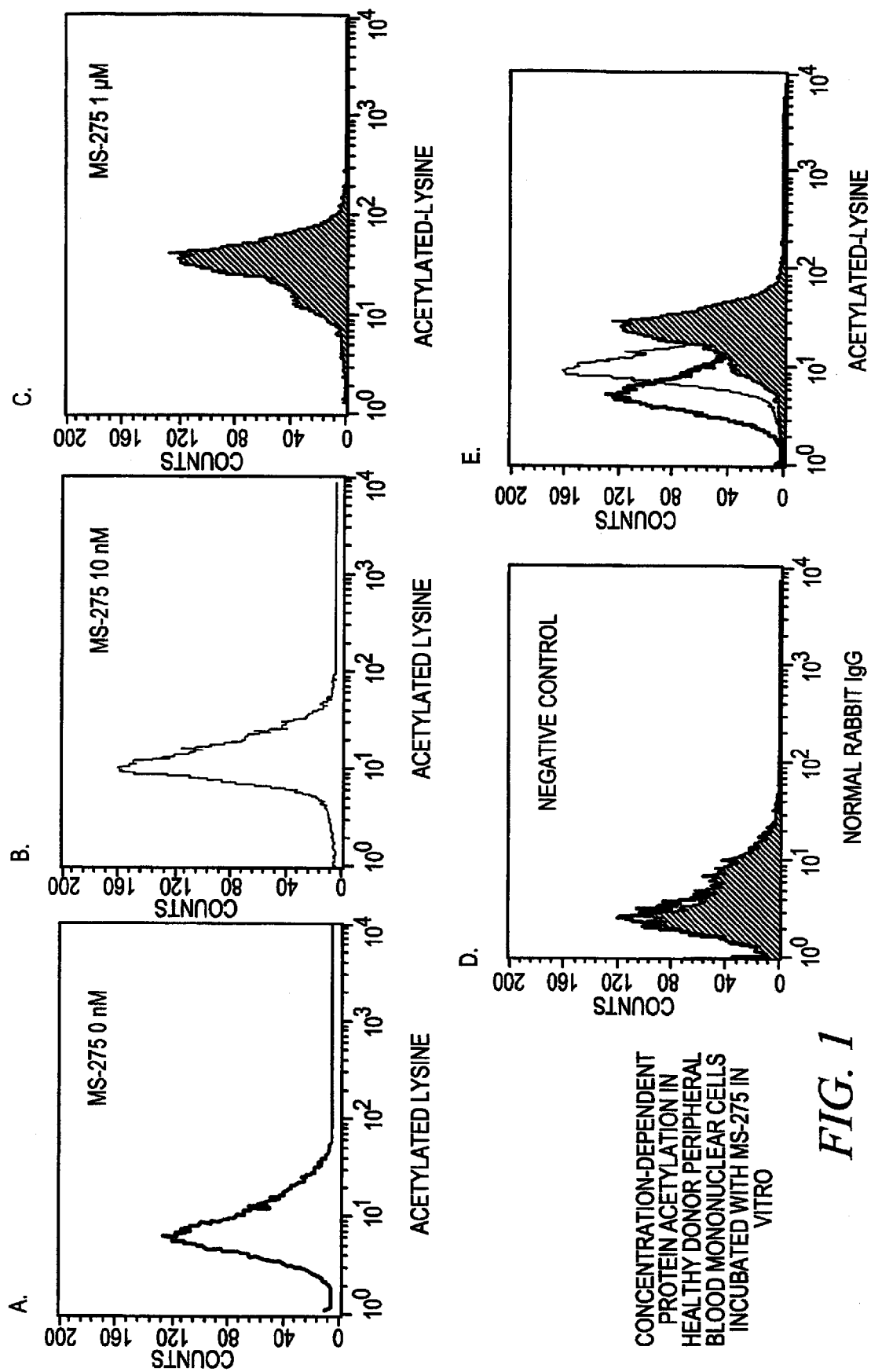

The invention provides methods for screening mixed cell samples for a pharmacodynamic response to one or more drugs. In one embodiment, the invention provides methods for screening mixed cell samples for the degree of protein acetylation in the cell samples. As little as 25 to 150 microliters of whole blood (e.g., obtained by a finger prick) can be quickly screened to determine and/or to quantify the pharmacodynamic response. Cell samples exposed in vivo or in vitro to one or more drugs can effectively be tested for their pharmacodynamic responses thereto using the methods of the invention. No separation of cell types in the whole blood samples prior to detecting the pharmacodynamic response is needed, or is generally desirable, for the practice of the invention.

The methods of the invention are simple. Many of the steps require little or no technical expertise or expensive equipment. Hence, the methods of the invention can be used for large scale screening procedures where many samples can be collected in the field and then processed at a convenient location such as a hospital or clinical laboratory.

Assay Methods

The invention provides methods for detecting and/or quantifying the pharmacodynamic response of mixed cell populations to one or more drugs. The effects of several drugs on a population of cells can readily be observed at once. The methods of the invention generally involve obtaining a cell sample, fixing the cells, permeabilizing the cells, reacting the cells with one or more reagents that reflect a pharmacodynamic response of the cells to the selected test agent(s) or drug(s) and using cell cytometry to observe and/or quantify the pharmacodynamic response of the cells to the test agent(s) or drug(s).

In one embodiment, the methods of the invention are used for detecting and/or quantifying protein acetylation in mixed populations of cells. The pharmacodynamic effect and/or the degree of protein acetylation can be correlated with other factors such as the cell cycle, cell differentiation, cell type or apoptosis, simply by staining the cells during the present methods using available markers for various stages of the cell cycle, cell differentiation, different cell types or for apoptosis.

The methods of the invention can be performed on many different cellular samples, for example, blood, bone marrow aspirates, isolated cell lines, tissue biopsies, cerebrospinal fluid, lymph, skin scrapings, tumor biopsy samples, fluids extracted from physiological tissues and the like. However, in many embodiments, the sample collected and tested is whole blood. Whole blood is preferably used for several reasons. First, whole blood has a variety of cell types which, according to the invention, reflect the physiological state of the donor and his or her response to drugs or to the environment. Second, the inventors have determined that only small amounts (e.g. 25-150 microliters) of whole blood are needed for accurate assessment of pharmacodynamic responses. Third, whole blood is easily obtained. No sophisticated equipment or technical expertise is required to collect the small amounts needed. No purification (e.g. no Ficoll gradient separation) of different cell types is typically performed. Numerous small blood samples can quickly be collected in the field for testing later at a more convenient location.

Samples from mammals and birds may be obtained for use the methods of the invention. Such mammals and birds include humans, mice, rats, dogs, cats, horses, cattle, sheep, goats, chickens, turkeys and the like. Animals are contemplated for initial testing or screening studies such as toxicology studies, dosage testing and other studies that facilitate drug development.

Small samples of mixed cell populations can be collected using standard procedures for collecting biological samples. Because only small amounts of cell samples are needed, a finger prick can provide sufficient whole blood for practice of the invention. Blood samples from the finger, arm, leg or any other site can be used. Animal blood samples are collected by procedures available in the art. If bone marrow aspirates, biopsies or tissue samples are to be tested, these samples are also obtained by standard procedures. Again, because only small numbers of cells are needed, just a small proportion of the total bone marrow aspirate, biopsy or tissue sample may be needed for performing the present methods. The rest can be reserved for other types of testing or for any other purpose contemplated by one of skill in the art.

After collection of the samples, the cells should be stabilized by fixation. In some instances one of skill in the art may choose to remove extracellular materials from the cells prior to fixation. However, such removal may not be necessary and factors loosely associated with the cell surface may be lost. Hence, one of skill in the art may frequently choose to skip such a cell washing step. If one of skill in the art chooses to wash the cells, for example, because only intracellular pharmacodynamic markers are of interest, washing can be performed by standard procedures such as by centrifuging the cells in an appropriately buffered saline solution. Bovine serum albumin (BSA), or other stabilizing material, can be added to the buffered saline solution during such a washing procedure. Washing the cells generally involves suspending the cells in the buffered saline solution, centrifuging the cells into a pellet, removing the supernatant and re-suspending the cells in the buffered saline solution. Several rounds of such washing can be performed if one of skill in the art chooses.

The cells are gently fixed in an available fixative for a time and under conditions sufficient to stabilize the cells. Fixative solutions generally contain a fixative in an appropriately buffered saline solution without any BSA or other such materials. Fixatives that can be used include dilute solutions of paraformaldehyde, for example, solutions of about 0.1% to about 4% paraformaldehyde. In some embodiments, the fixative solution is 0.4% paraformaldehyde in phosphate buffered saline. Generally, only short periods of time are required for fixation, for example, fixation can be for about 2 minutes to about 20 minutes. Fixation is done at mild temperatures, for example, at about 4° C. to about 42° C. When cooler temperatures are employed, longer fixation times are required; shorter fixation times are used when higher temperatures are employed. In some embodiments, fixation is at 37° C. for about 5 minutes to about 10 minutes. The cells are then washed in buffered saline solution as described above. After fixation, the cells can be stored at various temperatures, including room temperature or temperatures of about 4° C., until it is convenient for one of skill in the art to assess a pharmacodynamic response in the cells.

Cells can be gently permeabilized prior to reaction with many available reagents that detect a pharmacodynamic response. In general, such permeabilization is performed using a mild detergent in a buffered saline solution for a time and under appropriate conditions for gently permeabilizing the cells. For example, the permeablization solution can include small amounts of Triton X-100 in phosphate buffered saline. Amounts ranging from about 0.1% to 1% Triton X-100 can be used. In some embodiments, the permeabilization solution is a solution of 0.4% Triton X-100 in phosphate buffered saline. Permeabilization is for short periods of time at mild temperatures. For example, permeabilization can be performed for about 2 minutes to about 10 minutes at temperatures ranging from about 10° C. to about 37° C. In some embodiments, permeabilization is performed for about 5 minutes at room temperature. After permeabilization, the cells are washed in buffered saline as described above. Small amounts of BSA (e.g. 0.1% BSA) can be included in the wash solution at this stage.

Cells are exposed to a selected reagent that can detect a pharmacodynamic response. Such a reagent is any reagent that can selectively detect any pharmacodynamic marker known to one of skill in the art where the marker reflects a cellular response to a drug or to the environment. The reagent can be antibody, an enzyme, an enzyme substrate, an mRNA or other detectable substance. Examples of pharmacodynamic markers that can detect a pharmacodynamic response include protein acetylation, cancer markers, tubulin acetylation and the like.

In one embodiment, the reagent that can detect a pharmacodynamic response can detect protein acetylation. In many embodiments, the acetylation detection reagent can generally detect acetylation of lysine residues in substantially all types of proteins. The use of a reagent that detects acetylation of lysine residues in substantially all types of proteins permits detection of the spectrum of nuclear and cytoplasmic proteins that can be acetylated. Over forty proteins can be acetylated in eukaryotic cells, including histones, p53, tubulin, c-jun and the like. Many of these proteins perform crucial functions. For example, transcriptionally silenced chromatin, such as heterochromatin and inactivated mammalian X chromosomes, are associated with hypoacetylated histones. In contrast, transcriptionally active domains in euchromatin are often associated with histone hyperacetylation. According to the invention, the acetylation levels of such a spectrum of potentially acetylated proteins provides a measure of the sample donor's physiological state, response to drugs, disease progression and the like. Hence, the assay methods of the invention can be used for monitoring a patient's physiological state, disease progress and/or drug response over time by monitoring the acetylation of a spectrum of proteins.

Hence, any reagent that can detect acetylation in substantially any protein can be employed in the methods of the invention. One example of a reagent that can detect acetylation of lysine residues within proteins is an anti-acetylated lysine antibody preparation. Such anti-acetylated lysine antibodies are available to one of skill in the art. For example, such anti-acetylated lysine antibodies can be obtained from Cell Signaling Technology (Beverly, Mass.), Upstate Cell Signaling Solutions (Charlottesville, Va.), Novus (Littleton, N.Y.), Abcam (Cambridge, Mass.) or New England Biolabs (Beverly, Mass.). If one of skill in the art wishes to ascertain which protein is acetylated, a number of antibodies to specific acetylated proteins are available, including antibodies to specific acetylated histones, to acetylated tubulin (a marker for Taxol pharmacodynamic responses), and the like. Such specific antibodies can also be used in the inventive procedures.

The cells are exposed to the reagent that can detect a pharmacodynamic response for a time and under conditions sufficient for reaction between the reagent and the pharmacodynamic marker. Hence, cells can be suspended in a small volume of buffered saline, which can contain 0.1% BSA, and then mixed with an appropriate amount of the reagent. The cells are then incubated at mild temperatures for several minutes to several hours. For example, the cells can be incubated with anti-acetylated lysine antibodies at temperatures ranging from about 4° C. to about 37° C. for about 10 minutes to about 24 hours. In some embodiments, the cells are incubated with anti-acetylated lysine antibodies for about 1 hour at about room temperature. The cells are then washed as described above.

Many antibodies are directly attached to a detectable label so no further labeling reagents or secondary antibodies are needed. If a secondary reagent is desired or needed for visualization of the reagent that can detect a pharmacodynamic response, the cells are then reacted with this reagent. For example, the anti-acetylated lysine antibodies that are bound to acetylated lysine residues can be detected by use of an anti-mouse secondary antibody that binds to monoclonal anti-acetylated antibodies from mice. The secondary antibody can have a detectable label, such as a fluorescent dye, that can be followed and observed.

A variety of other reagents may be included in the screening assay. These include reagents like salts, neutral proteins, e.g. albumin, detergents, etc that are used to facilitate optimal protein-protein binding and/or reduce non-specific or background interactions.

After reaction with the selected reagents, the cells are analyzed by convenient methods, for example, by fluorimetry or flow cytometry. In some embodiments, detection of overall increases or decreases in signal from a selected label may be quantified by simple spectrophotometric or fluorometric means. However, for many embodiments, including those involving detection and/or quantification of multiple markers, flow cytometry is used. Flow cytometry, cell sorting and cell analysis methods are available and are described in, for example, The Handbook of Experimental Immunology, Volumes 1 to 4, (D. N. Weir, editor) and Flow Cytometry and Cell Sorting (A. Radbruch, editor, Springer Verlag, 1992).

In general, cells are analyzed and sorted on a flow sorter based on the cells' tendency to scatter light forward (FSC) and to the side (SSC). Such cell signals reflect the cell type and may be detected and quantified. In each experiment, parameters are empirically established regarding the forward and side scatter properties. In general, the gain on the photomultiplier tubes detecting the forward-scattered light and the side-scattered light in each dimension is adjusted to distribute the array of signals from the cells across the channels available for analysis in a manner known to one skilled in the art. Under these circumstances a characteristic pattern is observed.

Pharmacodynamic response patterns can be further analyzed by staining the cells with labeled antibodies or other reagents that bind to a variety of markers. Markers that may be examined include cell-type specific markers, cell cycle staging markers, differentiation markers, markers that indicate the cell may undergo apoptosis and the like. Thus, the assay procedures of the invention can be adapted to include a step for staining the cells with selected antibodies or other reagents that provide information as to cell type, differentiation, stage of the cell cycle and the like. In general, detection of such markers can be performed by adding the relevant antibody or other reagent to the cell samples before or after fixation. The reagent that detects a selected marker can be reacted with the cells before, after or during reaction of the cells with the reagent that detects the pharmacodynamic response. The various markers and different cell types can be detected using flow cytometry. Hence, parameters such as the type of cell that exhibits a pharmacodynamic response, the stage in the cell cycle of that cell, the differentiation stage, the likelihood of that cell to undergo apoptosis and the existence of primary pharmacodynamic markers can be assessed simultaneously.

Where the assay is a binding assay, one or more of the antibodies or other reagents that bind to a variety of pharmacodynamic markers may be joined to a label, where the label can directly or indirectly provide a detectable signal. Various labels include radioisotopes, fluorescers, chemiluminescers, enzymes, particles, e.g. magnetic particles, and the like. Such labels include pairs of molecules that can bind to each other, such as biotin and streptavidin, digoxin and antidigoxin, and the like. One member of such a pair of molecules can be attached to a label that permits detection of the pair, and any pharmacodynamic or other marker to which they are attached.

For example, apoptosis can be assayed by detecting TUNEL (TdT-mediated dUTP nick-end labeling) labeling of the 3'-OH free end of DNA fragments produced during apoptosis (Gavrieli et al. (1992) J. Cell Biol. 119:493). TUNEL assays generally consist of catalytically adding a nucleotide, which has been conjugated to a chromogen system or to a fluorescent tag, to the 3'-OH end of the 180-bp (base pair) oligomer DNA fragments in order to detect the fragments. The presence of a DNA ladder of 180-bp oligomers is indicative of apoptosis. Procedures to detect cell death based on the TUNEL method are available commercially, e.g., from Boehringer Mannheim (Cell Death Kit) and Oncor (Apoptag Plus).

Another apoptosis marker that is currently available is annexin, sold under the trademark APOPTEST™. The annexin marker is used in the "Apoptosis Detection Kit," which is also commercially available, for example, from R&D Systems. During apoptosis, a cell membrane's phospholipid asymmetry changes such that the phospholipids are exposed on the outer membrane. Annexins are a homologous group of proteins that bind phospholipids in the presence of calcium. A second reagent can be used in conjunction with the reagent that detect annexin, propidium iodide (PI), which is a DNA binding fluorochrome. When a cell population is exposed to both reagents, apoptotic cells stain positive for annexin and negative for PI, necrotic cells stain positive for both, while live cells stain negative for both. Other methods of testing for apoptosis are known in the art and can be used in the methods of the invention.

Applications

The present invention provides assays involving methods to detect the pharmacodynamic response patterns of mixed populations of cells. These assay methods can be used to detect and monitor a drug response in the individual from which the cells were obtained. Moreover, the assay methods of the invention can be used to detect and monitor drug responses in many people at once, or in a population of individuals over time. Because the sample size required for testing by the present methods is very small, the methods of the invention can be used for screening studies where the pharmacodynamic response patterns in many, many samples is quickly quantified. Hence, the methods of the invention have utility for clinical trials of drugs, for example, for phase I, II, III and IV clinical trials performed to obtain regulatory approval of a drug or a combination of drugs.

The methods of the invention can also be used to identify new drugs that elicit a desired pharmacodynamic response. The desired pharmacodynamic response can be any cellular response that is correlated with administration of a selected class of drugs. For example, in one embodiment, the screening methods of the invention can be used to identify agents that modulate a level of generalized protein acetylation in cells, the level of histone deacetylase enzymatic activity in cells or the level of tubulin acetylation in cells. Anti-acetylated lysine antibodies, anti-acetylated histone antibodies, anti-acetylated tubulin antibodies and the like can be used in such methods. In another embodiment, the screening methods of the invention can be used to identify test agents that modulate a level of Hsp70 expression, because certain anti-cancer drugs are known to increase Hsp70 expression. Hence, a test agent that increases Hsp70 expression is a candidate for further testing to ascertain whether that test agent has anti-cancer activity. Many such pharmacodynamic responses and pharmacodynamic markers are known to those of skill in the art. The invention contemplates use of the present methods for testing all such pharmacodynamic responses and for detecting all such pharmacodynamic markers.

Thus, the invention provides methods for identifying test agents that modulate a pharmacodynamic response in a eukaryotic cell. The term "modulate" encompasses an increase or a decrease in the measured pharmacodynamic response when compared to a suitable control. The method generally involves:

(a) contacting a mixed population of cells with a test agent to form a first test mixture;

(b) contacting the first test mixture with a reagent that can detect a pharmacodynamic response to form a second test mixture;

(c) subjecting the second test mixture to flow cytometry; and (d) observing whether the cells exhibit the pharmacodynamic response. An increase or a decrease in the pharmacodynamic response relative to a suitable control (e.g., a sample of the same mixed population of cells subjected to the method without exposure to the test agent) is an indication that the substance modulates a pharmacodynamic response. Another control could be, for example, a sample of the same mixed population of cells subjected to the method after being exposed to a drug that is known to produce the desired pharmacodynamic response. Test agents that increase or decrease a pharmacodynamic response to a desired extent may be selected for further study, and assessed for cellular cytotoxicity, biocompatibility, etc.

The terms "agent", "test agent", "substance" and "compound" are used interchangeably herein. Test agents encompass numerous chemical classes, typically synthetic, semi-synthetic, or naturally-occurring inorganic or organic molecules. Test agents may be small organic compounds having a molecular weight of more than 50 and less than about 2,500 daltons. Test agents may comprise functional groups necessary for structural interaction with proteins, particularly hydrogen bonding, and may include at least an amine, carbonyl, hydroxyl or carboxyl group, and may contain at least two of the functional chemical groups. The test agents may comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Test agents can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acetylation, acylation, alkylation, esterification, amidification, etc. to produce structural analogs.

In another embodiment, the effects of known, approved drugs on patients can be monitored by the methods of the invention. For example, deacetylase inhibitors are administered to treat cancer and other diseases in some patients, including children. The effects of such deacetylase inhibitors upon the patient can be monitored using the present methods by detecting general acetylation levels, tubulin acetylation levels or histone acetylation levels using the present methods. For example, the methods of the invention can be used to monitor the effects of deacetylase inhibitors such as MS-275, trichostatin A, trapoxin, sodium butyrate, apicidin, sodium phenylbutyrate, phenylacetate, depsipeptide, 3-bromopropionate, valproic acid, tributyrin, suberoylanilide hydroxamic acid (SAHA), m-carboxycinnamic acid bishydoxamic acid (CBHA), oxamfiatin, pyroxamide, CHAP, depsipeptide (FR901228 or more recently FK228), NVP-LAQ824, CI-994, PXD101 or apicidin-derived quinolone derivatives.

Similarly, the methods of the invention can be used to monitor the effects of known anti-cancer agents such 17-allylaminogeldanamycin (17-AAG) or imatinib (also called Gleevec).

Geldanamycin is an antibiotic that binds to Hsp90 and inhibits its adenosine triphosphate binding and activity as a chaperone. A derivative of geldanamycin is the Hsp90 inhibitor 17-allylaminogeldanamycin, which preferentially kills tumor cells and has been in phase I clinical trials. When 17-allylaminogeldanamycin regulates Hsp90 activity, the cell responds by increasing the levels of Hsp70. Hence, Hsp70 is a pharmacodynamic marker for the activity of 17-allylaminogeldanamycin. As illustrated herein, the pharmacodynamic response of cells to 17-allylaminogeldanamycin can be observed by observing the levels of Hsp70 using the methods of the invention. Such pharmacodynamic monitoring of 17-allylaminogeldanamycin can be performed with or without monitoring of other pharmacodynamic markers. For example, as shown herein, the levels of tubulin acetylation and/or overall cellular protein acetylation can be monitored simultaneously with the pharmacodynamic effects of 17-allylaminogeldanamycin.

Gleevec (imatinib mesylate) is approved to treat a rare cancer called Chronic Myeloid Leukemia (CML). Imatinib mesylate is a protein-tyrosine kinase inhibitor that inhibits the Bcr-Abl protein tyrosine kinase, which is made by the abnormal Philadelphia chromosome in chronic myeloid leukemia. The Bcr-Abl protein tyrosine kinase carries messages to the cell telling it to divide and grow. By blocking this message, imatinib mesylate prevents the cancer cells from making more cells and causes them to die by apoptosis. The chemical name for Gleevec (imatinib mesylate) is 4-[(4-Methyl-1-piperazinyl)methyl]-N-[4-methyl-3-[[4-(3-pyridinyl)-2-yrimidinyl]amino]-phenyl]benzamide methanesulfonate.

Hence, the invention provides a method of monitoring the pharmacodynamic response of a mixed population of eukaryotic cells to a selected drug. The method generally comprises:
  (a) contacting a mixed population of cells with a drug to form a first test mixture;
  (b) contacting the first test mixture with a reagent that can detect a pharmacodynamic response to the drug to form a second test mixture;
  (c) subjecting the second test mixture to flow cytometry; and
  (d) observing whether the cells exhibit the pharmacodynamic response. The method can further include quantifying the pharmacodynamic response of the cells to the drug. Such quantification can include calculating a proportionate increase or decrease in the pharmacodynamic response. For example, an increase or decrease in fluorescent signal during flow cytometry relative to one or more suitable controls can be used as a quantitative measure of the pharmacodynamic response. Such quantification can also include calculating what proportion of cells in the mixed population tested exhibit the pharmacodynamic response.

A suitable control can be, for example, a sample of the same mixed population of cells subjected to the method without exposure to the drug. Another control could be, for example, a sample of the same mixed population of cells subjected to the method after being exposed to a drug or test agent that is known to produce the desired pharmacodynamic response.

In another embodiment, the invention provides a method of monitoring the pharmacodynamic response of a mixed population of eukaryotic cells that have already been exposed to a selected drug, for example, in a patient receiving the drug as a result of treatment or during a clinical trial. The method generally comprises:
  (a) obtaining a mixed population of cells that have been exposed to a drug;
  (b) contacting the mixed population of cells with a reagent that can detect a pharmacodynamic response to the drug to form a second test mixture;
  (c) subjecting the second test mixture to flow cytometry; and
  (d) observing whether the cells exhibit the pharmacodynamic response.

In another embodiment, the assays of the invention are used to detect histone, p53 or tubulin acetylation as a marker for cancer development, cancer regression or cancer progression. Accordingly, the invention further provides methods of identifying a cancerous cell in a sample constituting a mixed population of cells, where the mixed population of cells is suspected of containing cancerous cells and non-cancerous cells. Of particular interest in some embodiments is the detection of tumors of lymphoid origin including, but are not limited to, hematological malignancies, such as childhood acute leukemia, non-Hodgkin's lymphomas, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, thymomas, and the like.

Hence, the invention provides a method of monitoring the progression or regression of cancer in a mixed population of eukaryotic cells. The method generally comprises:
  (a) obtaining a mixed population of cells from a patient;
  (b) contacting the mixed population of cells with a reagent that can detect acetylation of histones, tubulin or p53 to form a test mixture;
  (c) subjecting the test mixture to flow cytometry; and
  (d) observing whether the cells have increased or decreased levels of histone, tubulin or p53 acetylation. The method can further include quantifying the levels of acetylation over time. Such quantification can include calculating a proportionate increase or decrease in acetylation relative to previously observed levels in the patient or in patients having known cancers or known cancer stages. For example, an increase or decrease in fluorescent signal during flow cytometry relative to one or more suitable controls can be used as a quantitative measure of the pharmacodynamic response. Such quantification can also include calculating what proportion of cells in the mixed population tested exhibit the increases or decreases in acetylation.

In another embodiment, the invention provides methods for identifying whether a specific test agent or drug that modulate a pharmacodynamic response in a particular eukaryotic cell type. This method permits evaluation of effects of the test agent or the drug upon specific cell types. In this method, selected cell types or cell lines are tested for their response to the test agent or the drug. Such cell types can be purified from a mixed population of cells. Cell lines of a particular cell type can be obtained from cell depositories, for example, from the American Type Culture Collection (10801 University Blvd., Manassas, Va., 20110-2209 USA (ATCC)). The method generally involves:

(a) contacting a population of cells of a selected cell type with a test agent or drug to form a first test mixture;

(b) contacting the first test mixture with a reagent that can detect a pharmacodynamic response to form a second test mixture;

(c) subjecting the second test mixture to flow cytometry; and (d) observing whether the cells exhibit the pharmacodynamic response. An increase or a decrease in the pharmacodynamic response relative to a suitable control (e.g., a sample of the same population of cells subjected to the method without exposure to the test agent) is an indication that the substance modulates a pharmacodynamic response. Another control could be, for example, a sample of the same population of cells subjected to the method after being exposed to a drug that is known to produce the desired or expected pharmacodynamic response. Test agents that increase or decrease a pharmacodynamic response to a desired extent may be selected for further study, and assessed for cellular cytotoxicity, biocompatibility, etc.

In another embodiment, the invention provides assays for identifying whether a subject has or may develop an autoimmune disease. Histone deacetylase enzymes such as HDAC7 are expressed during T cell development at a time when T cells learn to distinguish self from non-self (thymic negative selection). Inappropriate HDAC7 activity could lead to selective dysregulation of the immune system such as autoimmune diseases or immune deficiencies. In the case of autoimmune diseases, such diagnostic assay is useful for diseases such as juvenile diabetes, multiple sclerosis, systemic lupus erythematosus, rheumatoid arthritis and other related disorders. Hence, the invention provides assays for identifying whether a subject has or may develop an autoimmune disease. Such methods involve detecting whether histone deacetylase activity is elevated in immune cells.

Kits

In another embodiment, the invention provides a kit for assaying cell samples according to the methods of the invention. The kit can have a reagent for detecting a pharmacodynamic response and instructions for using the reagent to detect and/or quantify the pharmacodynamic response in a mixed cell sample (e.g. blood). For example, the kit can have an anti-acetylated lysine antibody preparation for detecting protein acetylation. The kit can have anti-Hsp70 antibodies for detecting a pharmacodynamic response to an anti-cancer agent such as 17-AAG or imatinib mesylate. The kit can have anti-tubulin antibodies for detecting a pharmacodynamic response to taxol. The kit can have reagents for detecting apoptosis, for example, antibodies reactive with factors involved in the apoptosis pathway. Such apoptosis factors include, for example, poly(ADP-ribose)polymerase (PARP) and of capases 6, 7, 8 and 9. Hence, antibodies or other reagents reactive with these apoptosis factors can be used in the kits of the invention.

The kits of the invention can also have a container and a means for collecting samples. For example, the kits can have alcohol swabs, a syringe, a sharp object for pricking the skin and/or a capillary tube, vacutainer or other means for collecting blood from the finger, arm or other site. The kits can also have containers of solutions for fixing and permeabilizing cells within collected samples.

The present invention further pertains to a kit for collecting and stabilizing samples to be tested using the methods of the invention. The kit has a container and a means for collecting samples as described above, along with instructions for using the collecting means and the container for collecting samples. The kit can also contain a fixation solution for stabilizing the cells in the collected samples. This kit may be used in the field for collecting and stabilizing samples that will be tested by the methods of the invention at a convenient location.

The invention will be further described by reference to the following detailed examples, which are given for illustration of the invention, and are not intended to be limiting thereof.

Example 1

Detection of Acetylation in Whole Blood

This Example illustrates that acetylation of proteins in whole blood cells changes upon exposure of the cells to an acetylation inhibitor in vitro or upon administration of the deacetylase inhibitor in vivo. This assay can be used for large screening studies such as clinical trials because this assay requires only small amounts of blood, no purification of specific cell types is needed and the assay procedure is simple.

Materials and Methods

Peripheral whole blood samples of approximately 50-100 microliters in size were collected. After collection, whole blood samples were exposed to the deacetylase inhibitor MS-275 at concentrations varying from 0 to 1 micromolar. The MS-275 compound is N-(2-aminophenyl)-4-[N-(pyridin-3-ylmethoxycarbonyl)aminomethyl]benzamide. See, Saito et al., Proc. Natl. Acad. Sci. USA 96, 4592-4597 (1999). Blood cells were washed in wash buffer (phosphate buffered saline (PBS) containing 0.1% BSA).

In another series of experiments, the blood samples were obtained from a patient treated with the deacetylase inhibitor MS-275 at a dosage of 12 mg/m. Whole blood samples from this patient were obtained before MS-275 administration and then 24 hours after MS-275 treatment. Blood cells were washed in wash buffer (phosphate buffered saline (PBS) containing 0.1% BSA).

The different cell types were then fixed in fixation solution (0.4% paraformaldehyde in PBS), incubated at 37° C. for 5-10 minutes and washed with wash buffer. The fixed cells were then resuspended in permeabilization solution (0.4% Triton X-100 in wash buffer) and incubated at room temperature for 5 minutes. After washing with wash buffer, the fixed and permeabilized cells were resuspended in 100 microliters of wash buffer and incubated with anti-acetylated lysine antibodies for 1 hour at room temperature. Cells were then washed with wash buffer and incubated simultaneously with anti-CD3 antibodies conjugated with PE and secondary antibodies (FITC-labeled anti-mouse antibodies) for 1 hour at room temperature, then washed again in wash buffer. Fluorescence associated with the cells was detected and quantified by flow cytometry.

Results

Flow cytometry patterns for whole blood samples treated with MS-275 in vitro are provided in FIG. 1A-E. Comparison of FIG. 1A-E shows that treatment of blood cells with the MS-275 deacetylase inhibitor gives rise to a peak of cells that have increased acetylation. In other words, the fluorescence detected for the population of cells generally increases, indicating that more FITC-labeled acetylated lysine residues are present in samples that were treated with the deacetylase inhibitor. A shoulder can be seen on the peak in FIG. 1C, showing flow cytometer results for cells treated with 1 micromolar MS-275. This shoulder likely represents a sub-population of cells that responds differently to the deacetylase inhibitor. Alternatively, this shoulder may represent a sub-population of cells in a different part of the cell cycle or a sub-population of cells undergoing apoptosis. The procedures described in Example 2 that involve multi-parameter analyses can be used to analyze what types of cells exist in this shoulder and/or what types of cellular events are happening to cells in this shoulder.

Figure 2:
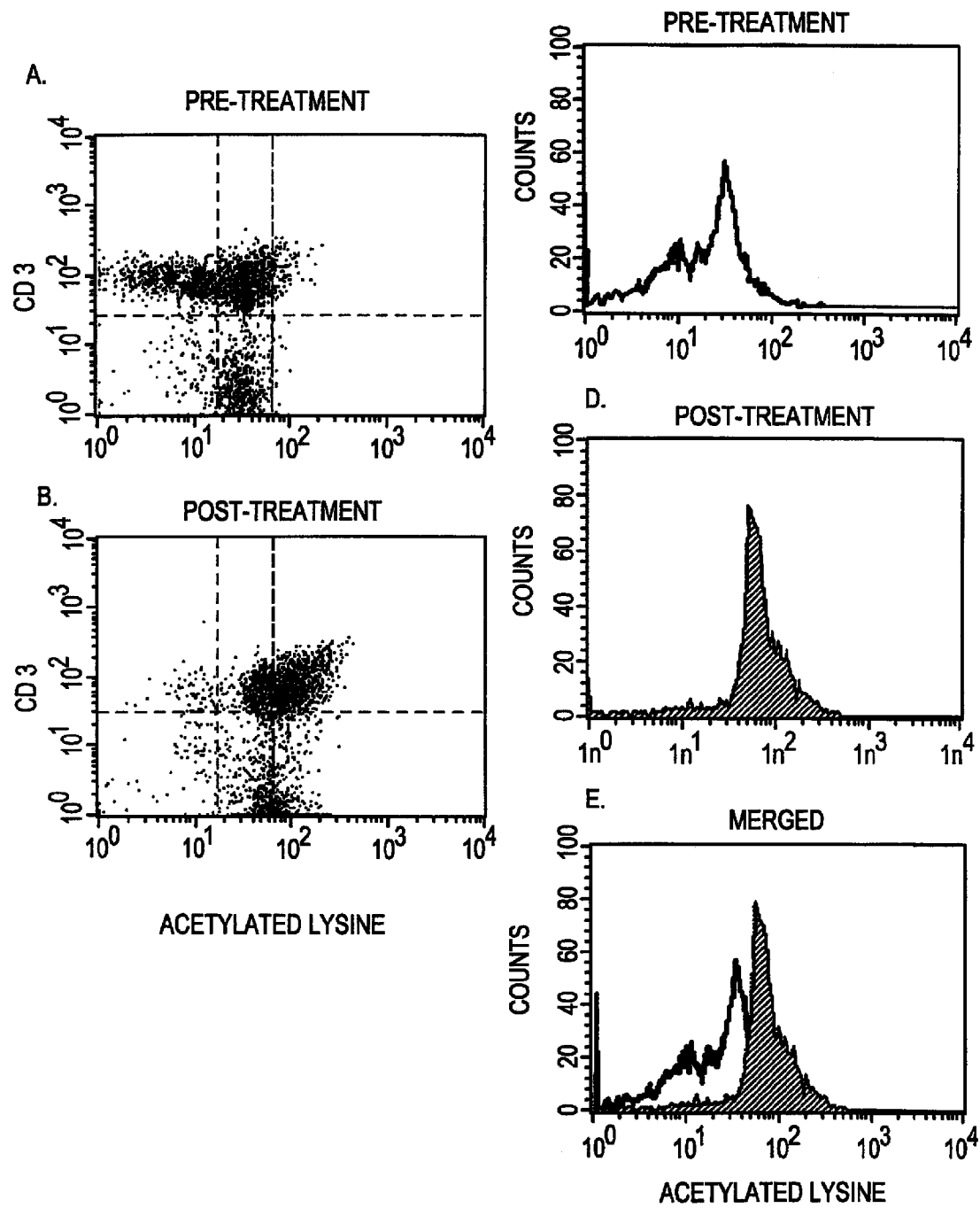

Flow cytometry patterns for whole blood samples obtained from a patient treated with MS-275 in vivo are provided in FIG. 2. As shown FIG. 2C-E, in vivo treatment of this patient with the MS-275 deacetylase inhibitor gives rise to a distinct peak of cells that have increased acetylation. Compared to the diffuse peak shown in FIG. 2C for non-treated cells, the post-treatment cells shown in FIG. 2D exhibit increased amounts of acetylated lysine. FIG. 2A-B show the fluorescence detected from CD3 labeled cells on the y-axis and the fluorescence detected from anti-acetylated lysine residues on the x-axis. As shown, there are positive and negative populations of CD3-positive cells: those that express CD-3 are T cells while non-T cells express no CD3 and form a smaller population of cells nearer the x-axis. Upon treatment with the MS-275 deacetylase inhibitor, the fluorescence for both populations of cells shifts to the right, indicating that both types of cells have increased acetylation. Hence, both T cells and non-T cells respond to the MS-275 deacetylase inhibitor.

Example 2

Protein Acetylation Patterns in Bone Marrow Aspirates

This Example illustrates that acetylation of proteins in bone marrow aspirates changes upon exposure of leukemia patients to a deacetylase inhibitor in vivo.

Materials and Methods

Bone marrow samples from a leukemia patient were collected before and 24 hours after administration of the MS-275 deacetylase inhibitor. Cells were washed in wash buffer (phosphate buffered saline (PBS) containing 0.1% BSA). The washed cells were resuspended in fixation solution (0.4% paraformaldehyde in PBS), incubated at 37° C. for 5-10 minutes and washed with wash buffer. The fixed cells were then resuspended in permeabilization solution (0.4% Triton X-100 in wash buffer) and incubated at room temperature for 5 minutes. After washing with wash buffer, the fixed and permeabilized cells were resuspended in 100 microliters of wash buffer and incubated with anti-acetylated lysine antibodies for 1 hour at room temperature. Cells were then washed with wash buffer and incubated with secondary antibody (FITC-labeled anti-rabbit antibodies) for 1 hour at room temperature, then washed in wash buffer. Fluorescence associated with the cells was detected and quantified by flow cytometry.

Results

Figure 3:
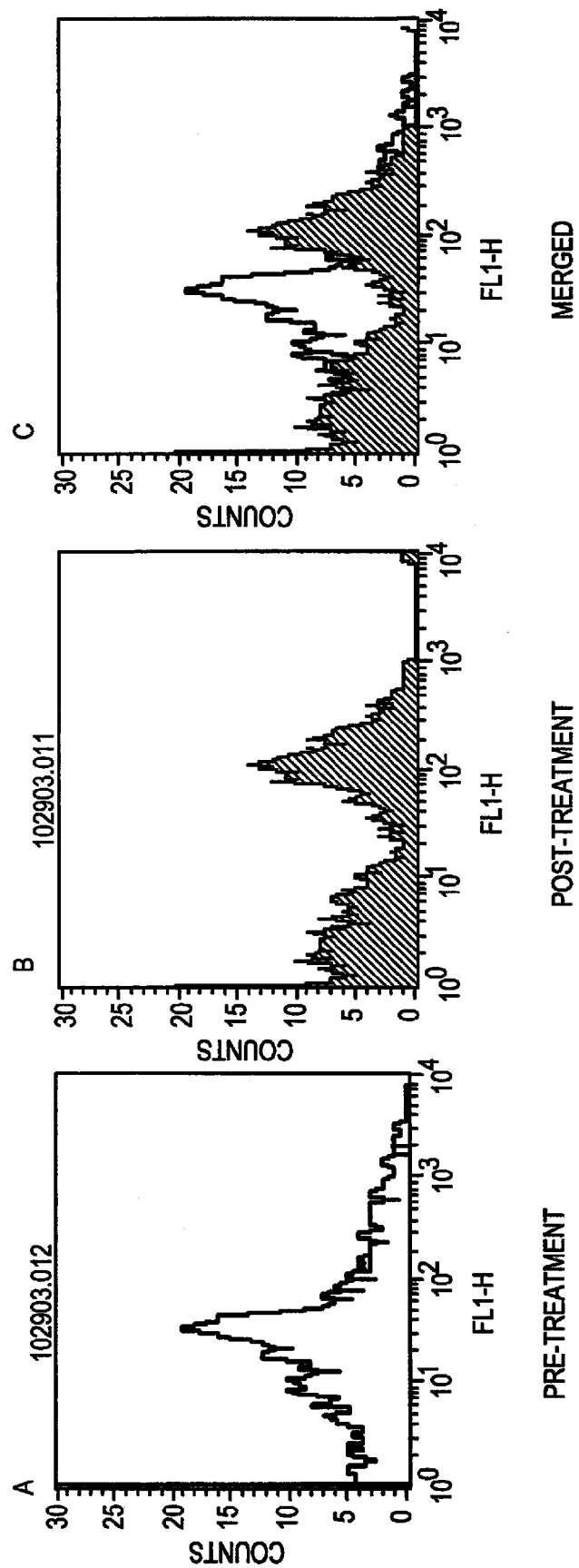

Flow cytometry patterns for bone marrow samples obtained from a leukemia patient treated with MS-275 in vivo are provided in FIG. 3. As shown in FIG. 3A, prior to in vivo treatment with MS-275, bone marrow cells comprise a broad peak of acetylated cells. However, after administration of the MS-275 deacetylase inhibitor, the bone marrow samples separate into two distinct peaks of cells (FIG. 3B). This is further illustrated by FIG. 3C, which shows both pre-treatment and post-treatment peaks. The presence of two post-treatment peaks may indicate that the treated sample is heterogeneous in some respect. For example, the tumor cells may be undergoing apoptosis as a result of treatment with the MS-275 deacetylase inhibitor. This hypothesis can readily be tested by labeling the cells with a marker for apoptosis and then observing whether the apoptosis marker associates with one or the other of the cell peaks detected after treatment with MS-275.

Example 3

Detection of Acetylation Simultaneously with Several Cell-Type Specific Markers

This Example illustrates that the procedures of the invention can be adapted to detect cell type specific markers in addition to acetylation of proteins in whole blood cells. These studies permit correlations to be made between the degree of acetylation and the cell type, the stage of the cell cycle, apoptosis or other factors.

Materials and Methods

Peripheral whole blood samples of approximately 50-100 microliters in size were collected and buffy coats were prepared by centrifugation of the anti-coagulated whole blood. Aliquots of these buffy coat samples were exposed to 1 micromolar MS-275 deacetylase inhibitor for 18 hour. Control aliquots of the buffy coat samples received no MS-275 deacetylase inhibitor. The cells were washed to remove the deacetylase inhibitor and resuspended in fixation solution (0.4% paraformaldehyde in PBS), incubated at 37° C. for 5-10 minutes and washed with wash buffer (PBS with 0.1% BSA). The washed cells were then resuspended in permeabilization solution (0.4% Triton X-100 in wash buffer) and incubated at room temperature for 5 minutes. After washing with wash buffer, the fixed and permeabilized cells were resuspended in 100 microliters of wash buffer and simultaneously incubated with antibodies to various cell type specific markers as well as anti-acetylated lysine antibodies for 1 hour at room temperature. The antibody markers employed were the B cell-specific CD19 marker (using a PE-Cy5 label), the T cell-specific CD3 marker (using a PE label), the granulocyte/monocyte CD15 marker (using a FITC label) and the monocyte-specific CD14 marker (using an APC-Cy7 label). Cells were then washed with wash buffer and incubated with secondary antibody (APC-labeled anti-rabbit antibodies) for 1 hour at room temperature, then washed in wash buffer. Fluorescence associated with the cells was detected and quantified by flow cytometry.

Results

Figure 4B:
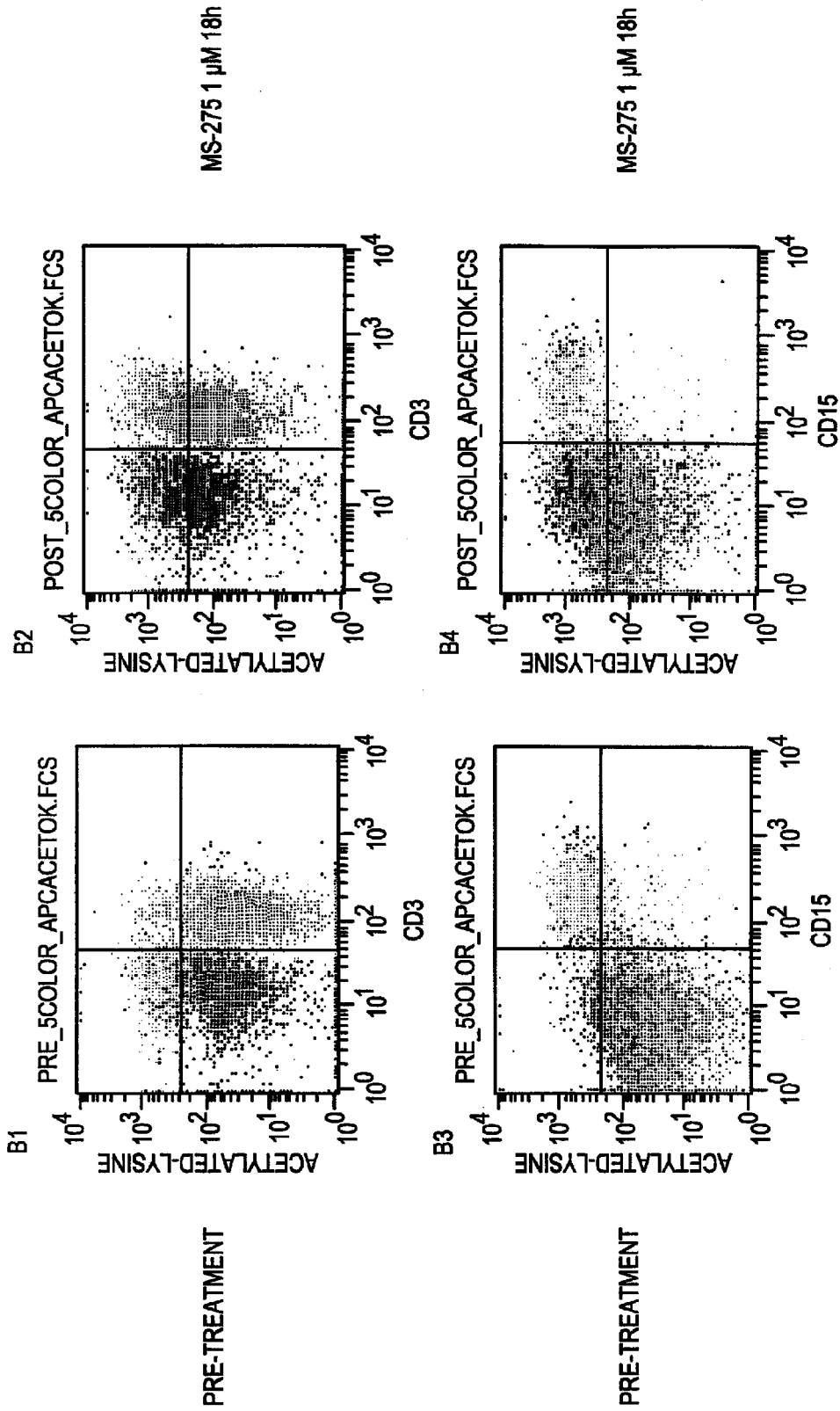
Figure 5:
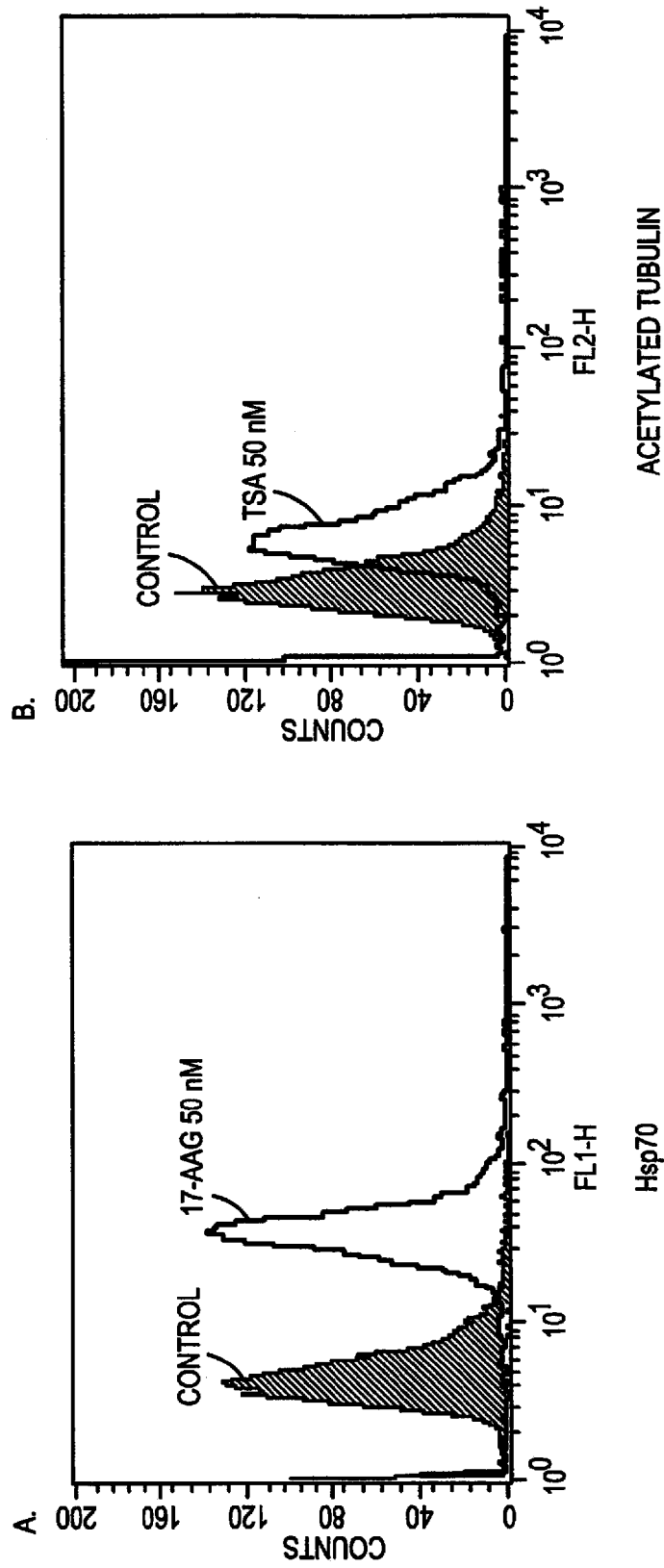

Flow cytometry patterns for samples that received no MS-275 are provided in FIG. 4A1-5. A scatter gram showing the forward (FSC-A) and side (SSC-A) light scattering of this population of cells is provided in FIG. 4A1. Each cell type exhibits a characteristic forward and side scatter pattern and the flow cytometer can be gated to detect and/or sort specific cell types by their scattering patterns. FIG. 4A2 shows the fluorescence colors associated with the fluorophore types on antibody preparations used to detect CD19, CD3, CD15 and CD14. FIG. 4A3-5 illustrate that the blood samples collected contain a variety of cell types that express different types of surface markers. As shown in FIG. 4A3, cells expressing the CD3 marker (darker shade at the top right; pink in the original) can be distinguished from those expressing the CD15 marker (lighter shade at the lower right; blue in the original). As shown in FIG. 4A5, cells expressing the CD14 marker (circled lighter shade at the top; green in the original) can be distinguished from those expressing the CD15 marker (circled darker shade at the lower right; blue in the original). The sample populations contained a significant proportion of T cells, as shown by detection of the CD3 marker, and a significant proportion of granulocytes and monocytes, as shown by detection of the CD14 and CD15 markers. None-the-less, the buffy coat samples collected contained a large number of different cell types.

Flow cytometric patterns for cell samples that received MS-275 treatment indicated that all cell types had increased acetylation after MS-275 treatment (see, FIG. 4B1-4). For example, comparison of FIGS. 4B1 and 4B3, with FIGS. 4B2 and 4B4 shows that the fluorescence due to acetylated lysine for essentially all cell types shifted upward, indicating that these cells had increased acetylation. Hence, essentially all of the blood cell types present in the samples collected responded to the MS-275 deacetylase inhibitor and exhibited increased acetylation. Therefore, samples collected from patients to test for drug effects need not be extensively purified before detection of the marker that identifies the drug effect.

Example 4

The Pharmacodynamics of Anti-Cancer Drugs and Deacetylase Inhibitors can be Monitored Simultaneously This Example illustrates that the procedures of the invention can be adapted to simultaneously detect the effects of two or more drugs on their pharmacodynamic markers. Previous methods relied upon western blot analysis, ELISA or immunocytochemical analysis. However, such procedures are cumbersome, time-consuming and cannot easily detect two or more events in a large population of cells. This Example illustrates that such multi-variable analysis can readily be performed using flow cytometry of small samples of blood.
Materials and Methods Leukemia K562 cell line samples containing approximately $5 \times 10^6$ to $1 \times 10^7$ cells were exposed to either the anti-cancer drug 17-allylaminogeldanamycin (17-AAG) or one of the deacetylase inhibitors MS-275 or trichostatin A (TSA). Some samples received both 17-AAG and TSA or both 17-AAG and MS-275. Control samples received no drug. Administration of the 17-AAG anti-cancer drug led to functional changes in Hsp90 and increased expression of Hsp70. Hence, the pharmacodynamic effect of 17-AAG can be detected by observing whether Hsp70 expression increases. TSA is a deacetylase inhibitor that can affect acetylation of numerous proteins. In this study, the effect of TSA on tubulin acetylation was observed using an antibody that specifically binds to acetylated tubulin.

After treatment with the various drugs, the cells were resuspended in fixation solution (0.4% paraformaldehyde in PBS), incubated at 37° C. for 5-10 minutes and washed with wash buffer. The fixed cells were then resuspended in permeabilization solution (4% Triton X-100 in wash buffer) and incubated at room temperature for 5 minutes. Cells were incubated for 1 hour at room temperature with antibodies to the various pharmacodynamic markers. Several cell samples were incubated with antibodies to several markers at once. These antibody preparations included antibodies to Hsp70 to detect the pharmacodynamic effect of 17-AAG and/or with anti-acetylated tubulin antibodies to detect the pharmacodynamic effect of the deacetylase inhibitors on tubulin acetylation and/or with anti-acetylated lysine antibodies to detect the general effect of deacetylase inhibitors on protein acetylation. The cells were then washed with wash buffer (PBS with 0.1% BSA) and incubated with secondary antibodies for 1 hour at room temperature, then washed in wash buffer. Fluorescence associated with the cells was detected and quantified by flow cytometry.
Results Flow cytometry patterns for samples that received 17-AAG or TSA are provided in FIG. 5A-B. As shown in FIG. 5A, cells receiving 17-AAG had increased levels of Hsp70 relative to control cells that received no 17-AAG. These results indicate that the cells are responding to the 17-AAG anti-cancer drug by increasing the synthesis of Hsp70. As shown in FIG. 5B, cells receiving TSA had increased levels of acetylated tubulin, indicating that the TSA deacetylase inhibitor has inhibited deacetylation of tubulin.

Figure 6:
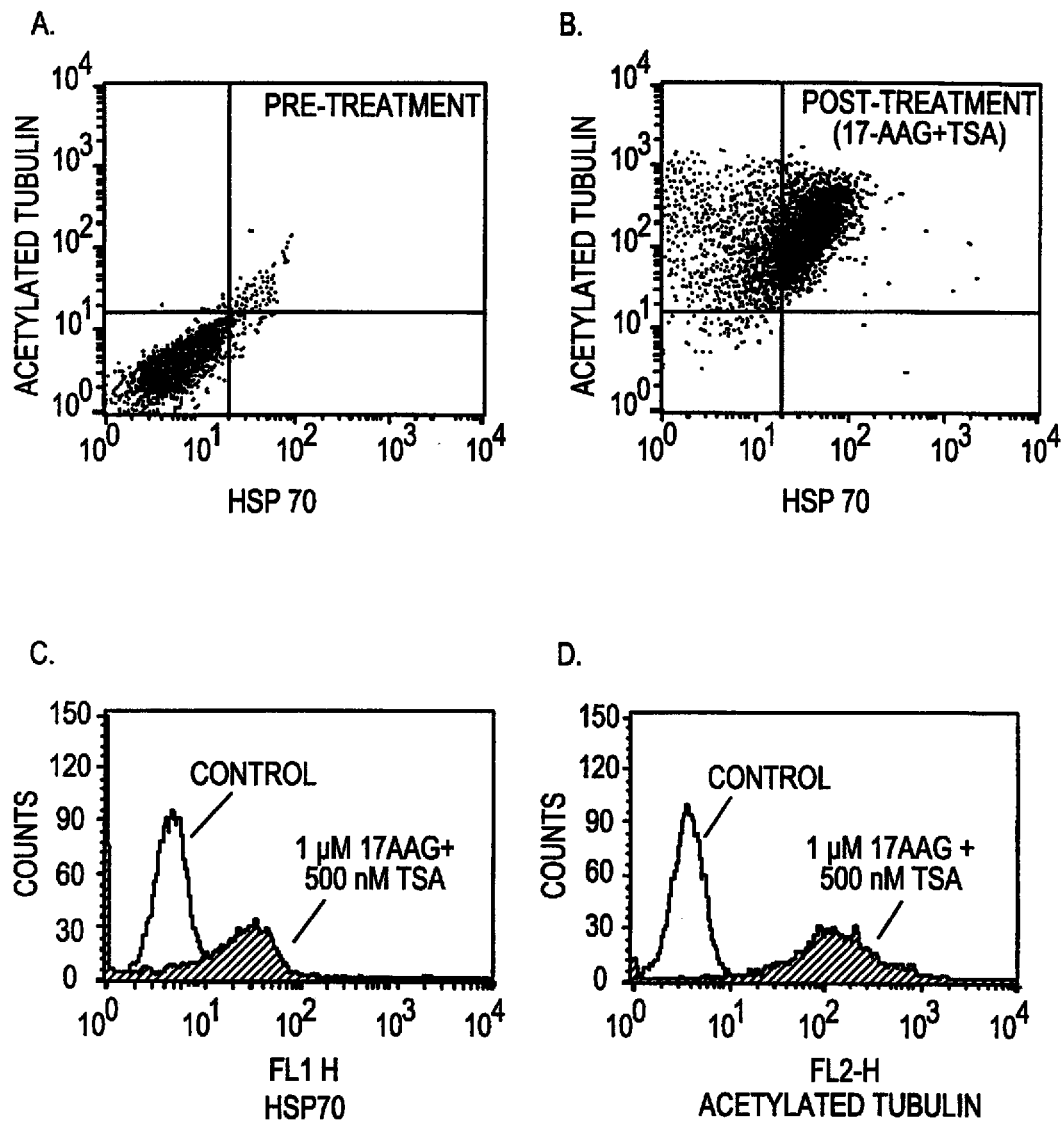
FIG. 6A-D illustrate that the pharmacodynamic effects of different drugs can be simultaneously monitored using the methods of the invention. The drugs employed were the anti-cancer drug 17-allylaminogeldanamycin (17-AAG) and the deacetylase inhibitor trichostatin A (TSA). As described above, the effects of 17-AAG were monitored by observing whether the levels of Hsp70 increased and the effects of TSA in this study were assessed by observing whether increased levels of tubulin acetylation occurred.

Flow cytometric results for the dual pharmacodynamic testing of the effects of both 17-AAG and TSA are shown in FIG. 6A-D. As shown in FIG. 6C-D, the levels of Hsp70 (C) and acetylated tubulin (D) both increased when these drugs were simultaneously administered. The dot plots in FIG. 6A-B show that only low levels of Hsp70 and acetylated tubulin are detected before drug administration (FIG. 6A). However, after exposure to 17-AAG and TSA, the levels of both Hsp70 and acetylated tubulin increase substantially (FIG. 6B). Hence, the pharmacodynamics of two drugs in a mixed population of cells were readily observed.

Figure 7:
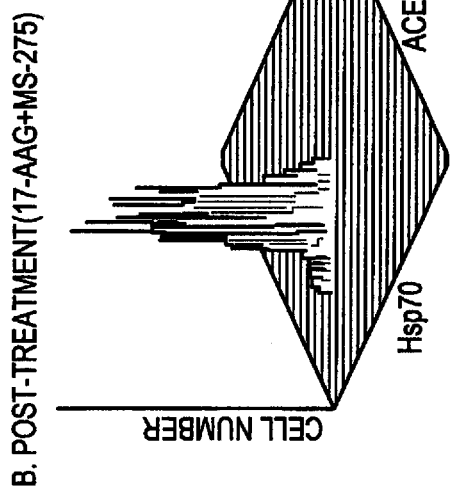
FIG. 7A-D illustrate that the pharmacodynamic effects of different drugs can be simultaneously monitored using the methods of the invention. The drugs employed were the anti-cancer drug 17-allylaminogeldanamycin (17-AAG) and the deacetylase inhibitor MS-275. As described above, the effects of 17-AAG were monitored by observing whether the levels of Hsp70 increased. The effects of MS-275 were assessed by observing whether increased levels of overall protein acetylation occurred.
Figure 7:
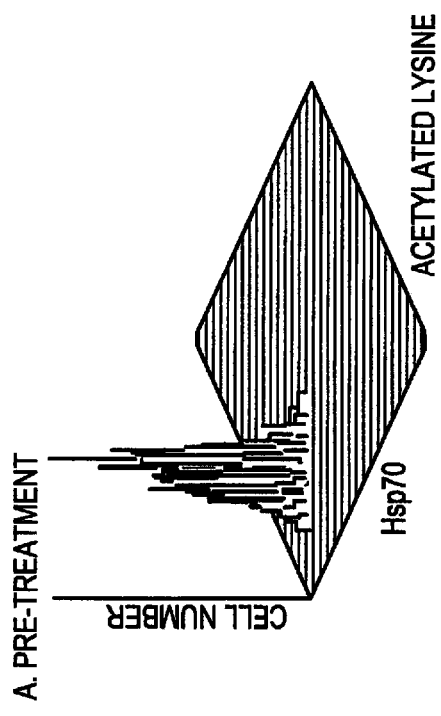
Figure 7:
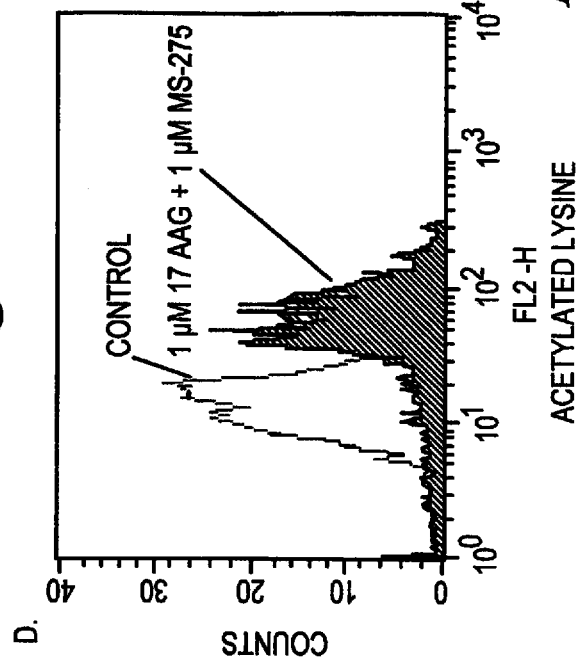
Figure 7:
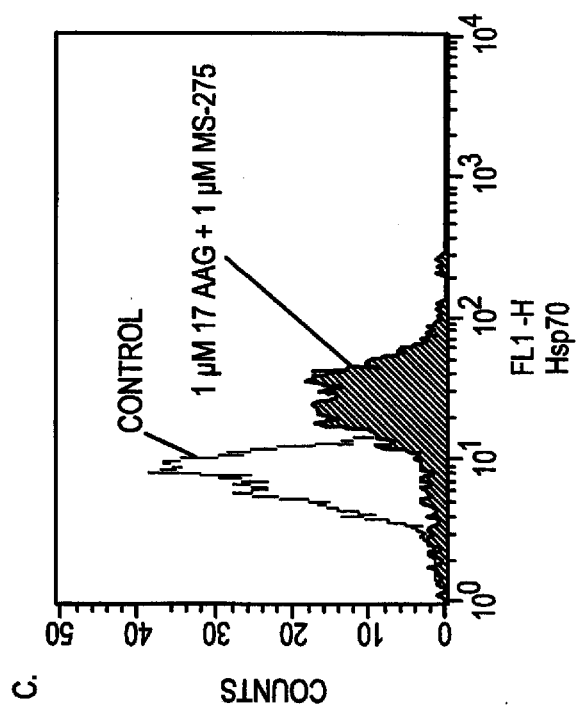

Flow cytometric patterns for the dual pharmacodynamic testing of the effects of both 17-AAG and MS-275 are shown in FIG. 7A-D. As shown in FIG. 7C-D, the levels of both Hsp70 (C) and acetylated lysine (D) increased when these drugs were simultaneously administered. The three dimensional maps shown in FIG. 7A-B show that only low levels of Hsp70 and acetylated lysine are detected before drug administration (FIG. 7A). However, after exposure to 17-AAG and MS-275, the levels of both Hsp70 and acetylated lysine increase substantially (FIG. 7B-D). Hence, the pharmacodynamics of two drugs in a mixed population of cells were readily observed.

Example 5

Immunocytochemical Analysis of Protein Acetylation

This Example uses deconvolution microscopy to illustrate that the staining procedure used in the flow assay can detect hyperacetylation of both nuclear and cytoplasmic proteins.
Materials and Methods Cells were pelleted onto glass slides by cytocentrifugation, stained as described above for flow cytometric analysis, counterstained with the fluorescent DNA dye DAPI, and viewed using a Leica DM IRB fluorescence microscope equipped with a Z-axis motor (Ludl Electronics, Hawthorne, N.Y.). Stacks of images (between 13 and 19 optical sections at a step size of 0.3 µm) were taken with a digital camera (Hamamatsu) and processed using Openlab Volume Deconvolution software (Improvision, Lexington, Mass.).

Results

Figure 8:
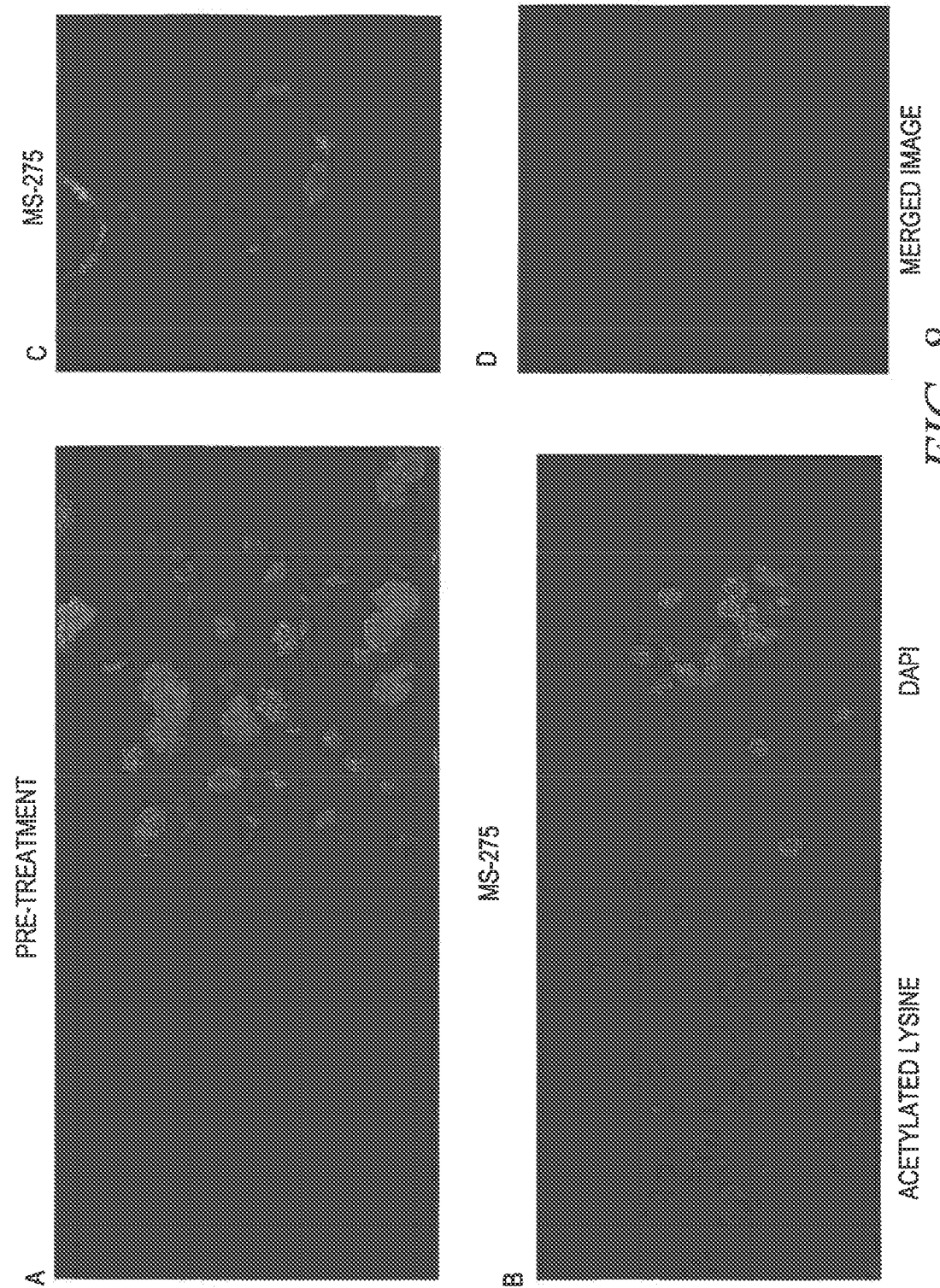
FIG. 8A-D provide an immunocytochemical analysis of protein acetylation. Healthy donor unfractionated buffy coats were treated with carrier only (FIG. 8A) or 1 µM MS-275 (FIG. 8B) for 24 hours, labeled with anti-acetylated lysine antibody, and nuclei were counterstained with DAPI.

To determine whether an antibody to acetylated lysine can be used to assess the response to HDAC inhibitors, and to assess if the response can be observed in both nuclear and cytoplasmic compartments, unfractionated buffy coats of healthy donors were incubated with the HDAC inhibitor MS-275 and examined for protein acetylation by immunocytochemistry. Untreated cells showed a variable level of acetylation that ranged from undetectable to moderate (FIG. 8A). In the majority of cells treated with MS-275 (1 µM, 20 hours), protein acetylation was markedly increased (FIG. 8B). Examination of MS-275-treated cells by optical sectioning demonstrated that both cytoplasmic and nuclear staining could be visualized, with considerable cell-to-cell heterogeneity in the localization of acetylated proteins. FIG. 8C displays a cell with predominantly nuclear signal and FIG. 8D shows a cell with predominantly cytoplasmic signal.

Example 6

Flow Cytometric Analysis of Apoptosis Versus Protein Acetylation

This Example illustrates that the multiparameter flow approach can be used to detect the correlation, at the single cell level, of protein hyperacetylation and the induction of tumor cell apoptosis in response to anticancer drug treatment.
Materials and Methods K562 chronic myelogenous leukemia cells were incubated with vehicle alone, 1 µM imatinib (the anticancer drug also known as Gleevec), 1 µM MS-275, or both for 48 hours. The cells were then stained for acetylated lysine as described above and co-stained with antibody to activated caspase 3 as an indicator of cells undergoing apoptosis. Dot plots display acetylated lysine on the x-axis and activated caspase 3 on the y-axis.
Results The multiparameter flow cytometric assay is a powerful tool to monitor pharmacodynamic changes induced by anti-cancer drugs used in monotherapy or combination therapy protocols. HDAC inhibitors have been reported to promote imatinib-mediated apoptosis in Bcr/Abl+ human myeloid leukemia cells, including imatinib-resistant cells. The effect of MS-275 and imatinib were therefore examined, alone and in combination, on apoptosis in the Bcr/Abl+ cell line K562. Because both MS-275 and imatinib have been reported to induce apoptosis associated with caspase 3 activation, an antibody was used that specifically recognizes activated caspase 3 in a flow assay. This caspase 3 flow assay effectively monitors drug-induced apoptosis. When combined detection of acetylated lysine, this flow assay permitted simultaneous monitoring of apoptosis (caspase 3) and acetylated lysine.

Figure 9:
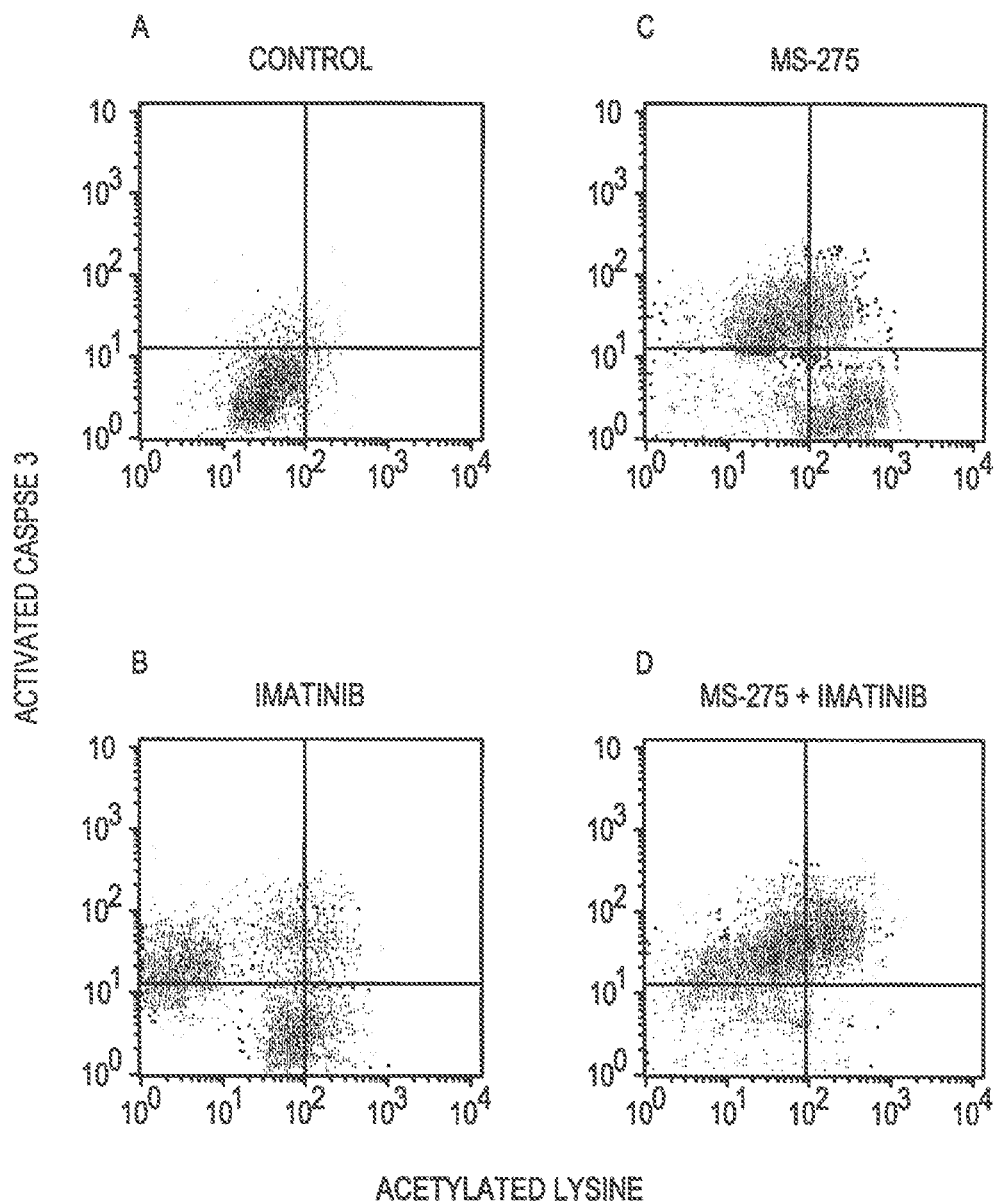
FIG. 9A-D illustrate that apoptosis and protein acetylation can be monitored simultaneously in cells treated with MS-275 (deacetylase inhibitor) and/or the anti-cancer agent imatinib. K562 cells were incubated with vehicle alone (FIG. 9A), 1 µM imatinib (FIG. 9B), 1 µM MS-275 (FIG. 9C), or both (FIG. 9D) for 48 h, and analyzed by multiparameter flow cytometry after reaction with antibodies directed against caspase3 and acetylated lysine. Dot plots display acetylated lysine on the x-axis and activated caspase 3 on the y-axis.

As can be seen in FIG. 9B-C, both MS-275 and imatinib increased the percent of apoptotic cells, and MS-275 strongly upregulated acetylation in over 50% of the cells. One population of cells lost acetylation when treated with imatinib (FIG. 9B) and these cells were positive for activated caspase 3. Furthermore, a population of non-apoptotic cells was present after treatment with either MS-275 or imatinib alone (cells clustered near the bottom of the FIG. 9B-C), and this population was almost eliminated by treatment with both MS-275 and imatinib.

These results demonstrate that hyperacetylation combined with the tyrosine kinase inhibitor imatinib is a highly effective treatment for chronic myelogenous leukemia cells.

Example 7

Figure 10:
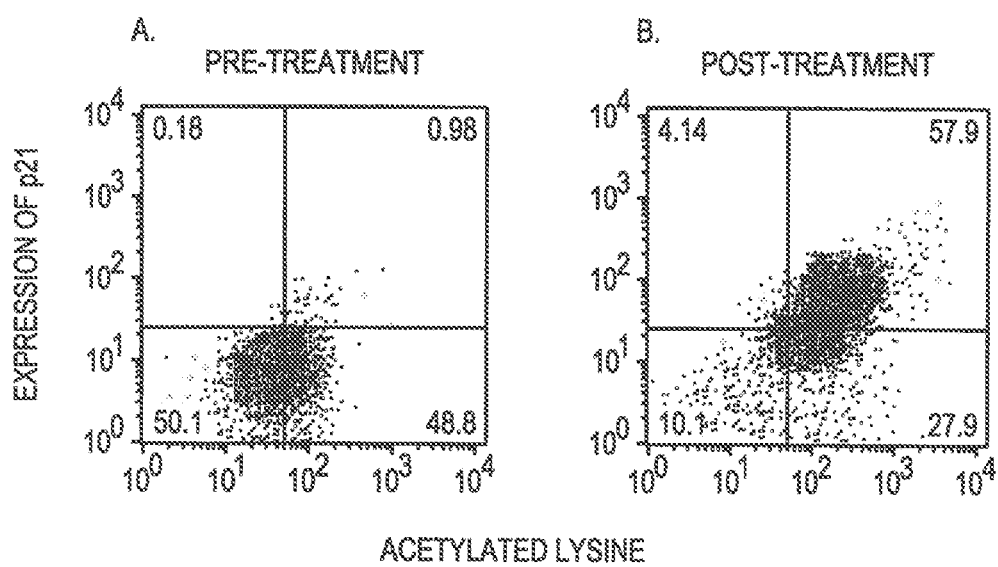
FIG. 10A-B illustrate p21 expression versus acetylated lysine in bone marrow aspirates in response to MS-275 in vivo. Bone marrow aspirates from a leukemia patient treated on a MS-275 protocol were analyzed by flow cytometry for expression of p21 versus protein hyperacetylation, pre-treatment (FIG. 10A) and post-treatment (FIG. 10B) with MS-275.

Detection of p21 Expression Versus Acetylated Lysine in Leukemia Patient Bone Marrow Aspirates in Response to MS-275 In Vivo This Example demonstrates that the multi-parameter flow assay can be used to monitor changes in protein expression in response to anticancer drug treatment, and that the effect of this treatment on protein expression can be correlated at the single cell level to treatment-induced protein hyperacetylation.
Materials and Methods Bone marrow aspirates were obtained and stained for acetylated lysine as described above. The cells were co-stained for the expression of the cyclin-dependent kinase inhibitor p21. The samples were then analyzed by multiparameter flow cytometry.
Results Histone deacetylase inhibitors can modulate the pattern of gene expression in tumor cells, and this modulation of gene expression may be critical to histone deacetylase inhibitor anti-tumor activity. One of the most important genes induced by HDAC inhibitors is the cyclin-dependent kinase inhibitor p21. As shown in FIG. 10A-B, there is a low level of protein acetylation and p21 expression prior to treatment of the patient with MS-275 (FIG. 10A). However, the level of both protein acetylation and p21 were clearly increased in response to treatment with MS-275 (FIG. 10B).

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of monitoring protein acetylation in a mixed population of eukaryotic cells exposed to a drug, comprising:
   a. obtaining a mixed population of cells from whole blood, bone marrow, or cerebrospinal fluid that has been exposed in vivo to a drug to form a first test mixture;
   b. contacting the first test mixture with a reagent that detects protein acetylation associated with total cellular lysine modifications in both nuclear and cytoplasmic proteins to form a second test mixture; and
   c. observing protein acetylation at the single cell level in the second test mixture by flow cytometry.

2. The method of claim 1, wherein the method further comprises quantifying the protein acetylation of the cells.

3. The method of claim 2, wherein quantifying the protein acetylation of the cells comprises calculating an increase or decrease in fluorescence signal during flow cytometry relative to one or more suitable controls.

4. The method of claim 3, wherein a suitable control is a sample of the same mixed population of cells subjected to the method without exposure to the drug.

5. The method of claim 3, wherein a suitable control is a sample of the same mixed population of cells subjected to the method after being exposed to a drug that is known to produce protein acetylation of the cells.

6. The method of claim 1, wherein the mixed population of cells is from human blood.

7. The method of claim 1, wherein the mixed population of cells is from animal blood.

8. The method of claim 1, wherein the mixed population of cells has a volume ranging from about 25 microliters to about 150 microliters.

9. The method of claim 1, wherein the reagent that can detect protein acetylation associated with cellular lysine modifications is an antibody that can bind to an acetylated protein.

10. The method of claim 9, wherein the antibody comprises a detectable label.

11. The method of claim 1, wherein the drug is a deacetylase inhibitor.

12. The method of claim 11, wherein the deacetylase inhibitor is MS-275, trichostatin A, trapoxin, sodium butyrate, apicidin, sodium phenylbutyrate, phenylacetate, depsipeptide, 3-bromopropionate, valproic acid, tributyrin, suberoylanilide hydroxamic acid (SAHA), m-carboxycinnamic acid bishydoxamic acid (CBHA), oxamflatin, pyroxamide, CHAP, depsipeptide (FK228), NVP-LAQ824, CI-994, PXD101, apicidin-derived quinolone derivatives or a combination thereof.

13. The method of claim 1, wherein the acetylated protein is acetylated tubulin.

14. The method of claim 1, wherein the drug is an anti-cancer drug.

15. The method of claim 14, wherein the anti-cancer drug is imatinib mesylate, 17-allylaminogeldanamycin or a combination thereof.

16. The method of claim 1, wherein the method further comprises observing which cell types exhibit protein acetylation.

17. The method of claim 1, wherein the method further comprises observing in what cell cycle stage the cells exhibit protein acetylation.

18. The method of claim 1, wherein the method further comprises observing whether some of the cells are undergoing apoptosis.

19. The method of claim 1, wherein the mixed population of cells has been exposed to more than one drug.

20. A method of identifying whether a test agent modulates protein acetylation in a mixed population of eukaryotic cells, comprising:
   a. obtaining a mixed population of cells from whole blood, bone marrow, or cerebrospinal fluid that has been exposed in vivo to a test agent to form a first test mixture;
   b. contacting the first test mixture with a reagent that detects protein acetylation associated with total cellular lysine modifications in both nuclear and cytoplasmic proteins to thereby form a second test mixture; and
   c. observing protein acetylation at the single cell level in the second test mixture by flow cytometry.

21. A method of monitoring protein acetylation in a sample of whole blood exposed to a drug, comprising:
   a. obtaining a sample of whole blood exposed in vivo to a drug to form a first test mixture;
   b. contacting the first test mixture with a reagent that detects protein acetylation associated with total cellular lysine modifications in both nuclear and cytoplasmic proteins to form a second test mixture; and
   c. observing protein acetylation at the single cell level in the second test mixture by flow cytometry.

22. The method of claim 1, wherein the method comprises quantitatively monitoring protein acetylation.

23. The method of claim 20, wherein the method comprises quantitatively monitoring protein acetylation.

24. The method of claim 21, wherein the method comprises quantitatively monitoring protein acetylation.

25. The method of claim 1, wherein the method further comprises fixing the cells.

26. The method of claim 20, wherein the method further comprises fixing the cells.

27. The method of claim 21, wherein the method further comprises fixing the cells in the whole blood sample.

28. The method of claim 20, wherein the mixed population of cells has a volume ranging from about 25 microliters to about 150 microliters.

29. The method of claim 21, wherein the sample has a volume ranging from about 25 microliters to about 150 microliters.

30. A method of monitoring protein acetylation in a mixed population of eukaryotic cells exposed to a drug, comprising:
   a. obtaining a mixed population of cells that has been exposed in vivo to a drug to form a first test mixture;
   b. contacting the first test mixture with a reagent that can detect protein acetylation associated with total cellular lysine modifications to both nuclear and cytoplasmic proteins to form a second test mixture; and
   c. observing protein acetylation at the single cell level in the second test mixture by flow cytometry.

31. A method of identifying whether a test agent modulates protein acetylation in a mixed population of eukaryotic cells, comprising:
   a. obtaining a mixed population of cells that has been exposed in vivo to a test agent to form a first test mixture;
   b. contacting the first test mixture with a reagent that can detect protein acetylation associated with total cellular lysine modifications to both nuclear and cytoplasmic proteins to thereby form a second test mixture; and
   c. observing protein acetylation at the single cell level in the second test mixture by flow cytometry.

* * * * *